(12) United States Patent
Stowasser et al.

(10) Patent No.: US 8,119,841 B2
(45) Date of Patent: Feb. 21, 2012

(54) CRYSTALLINE FORMS OF ALISKIREN HEMIFUMARATE

(75) Inventors: Frank Stowasser, Murg (DE); Stephanie Monnier, Raedersheiim (FR)

(73) Assignee: Novartis AG, Basel (CH)

( * ) Notice: Subject to any disclaimer, the term of this patent is extended or adjusted under 35 U.S.C. 154(b) by 323 days.

(21) Appl. No.: 12/312,320

(22) PCT Filed: Nov. 5, 2007

(86) PCT No.: PCT/EP2007/009573
§ 371 (c)(1), (2), (4) Date: May 5, 2009

(87) PCT Pub. No.: WO2008/061622
PCT Pub. Date: May 29, 2008

(65) Prior Publication Data
US 2010/0048716 A1    Feb. 25, 2010

(30) Foreign Application Priority Data
Nov. 7, 2006 (EP) .................................. 06123642

(51) Int. Cl.
*C07C 237/14* (2006.01)
*A61K 31/16* (2006.01)

(52) U.S. Cl. ........................ 564/155; 514/616

(58) Field of Classification Search ........................ None
See application file for complete search history.

(56) References Cited

U.S. PATENT DOCUMENTS
5,559,111 A * 9/1996 Goschke et al. .......... 514/227.5
6,730,798 B2 * 5/2004 Stutz et al. .................... 549/323

FOREIGN PATENT DOCUMENTS
| EP | 0 678 503 | 4/1995 |
| WO | 02/02508 | 1/2002 |
| WO | 2006/024501 | 3/2006 |

OTHER PUBLICATIONS
David A. Sandham, et al., "A convergent synthesis of the renin inhibitor CGP60536B," Tetrahedron Letters 41 (2000), Elsevier, Amsterdam, 10091-10094.
Harry G. Brittain, "Polymorphism in pharmaceutical solids", Marcel Dekker, DJW Grant (Cp1), pp. 1-10, and J,K, Guillory (Chapter 5), pp. 183-226, 1999.

* cited by examiner

*Primary Examiner* — Brian J Davis
(74) *Attorney, Agent, or Firm* — Lisa Matovcik

(57) ABSTRACT

This invention relates to crystal forms of aliskiren hemifumarate and various embodiments related thereto, e.g. pharmaceutical preparations, processes for the manufacture of the crystal forms, pharmaceuticals uses and the like. The crystal forms have particularly advantageous properties e.g. they are useful in the manufacture of blood-pressure lowering pharmaceutical preparations and the like.

23 Claims, 12 Drawing Sheets

CRYSTALLINE FORMS OF ALISKIREN HEMIFUMARATE

Figure 1:
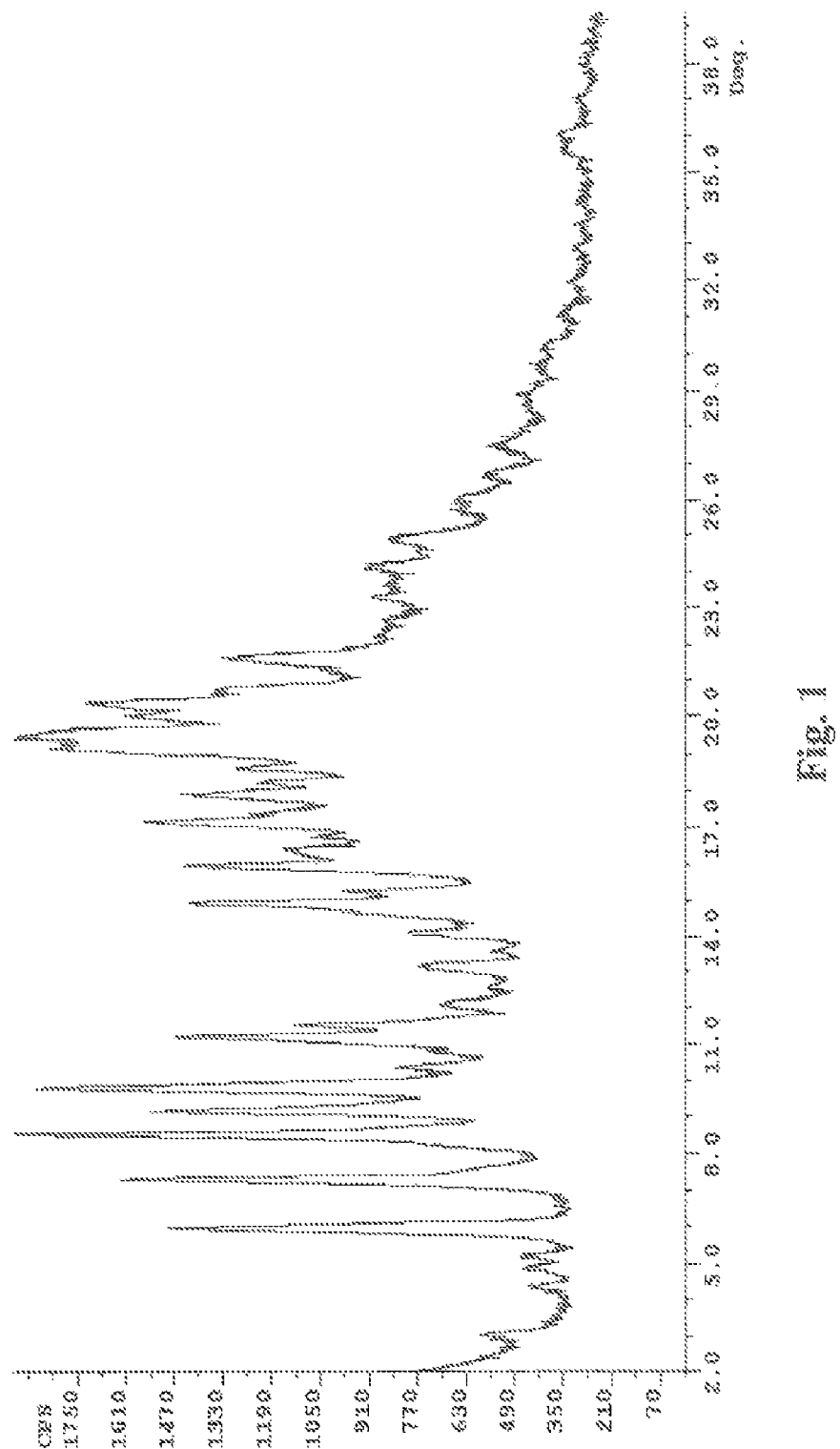

This application is a National Stage of International Application No. PCT/EP2007/009573 filed on Nov. 5, 2007, the entire disclosure of which is hereby incorporated by reference.

SUMMARY OF THE INVENTION

This invention relates to novel crystal (including solvate) forms of aliskiren hemifumarate and to pharmaceutical preparations comprising them and methods of their manufacture, as well as the use of said crystal forms or preparations in the treatment of various diseases and disorders, and related invention embodiments presented in detail below.

BACKGROUND OF THE INVENTION

The renin-angiotensin system (RAS) plays an important role in the regulation of blood pressure (BP) and volume homeostasis. Renin is secreted by the kidney in response to a decrease in circulating volume and blood pressure, and cleaves the substrate angiotensinogen to form the inactive decapeptide Angiotensin I (Ang I). Ang I is converted in the lungs, the kidneys and other organs to form the active octapeptide Ang II by the angiotensin converting enzyme (ACE). Ang II interacts with cellular receptors inducing vascular constriction, the release of catecholamines from the adrenal medulla and pre-junctional nerve endings. It also promotes aldosterone secretion and sodium reabsorption. In addition, Ang II inhibits renin release, thus providing a negative feedback to the system. Ang II acts at various levels (e.g. vasculature, sympathetic nervous system, cortex and medulla of the adrenal gland) to increase vascular resistance and BP.

The RAS may be blocked at various levels. Angiotensin II receptor blockers act on the RAS by inhibiting the interaction between Ang II and the $AT_1$ receptor. ACE inhibitors block the conversion of Ang I to Ang II and potentiate bradykinin. Renin inhibitors block the RAS at an earlier point in the cascade than ACE inhibitors and have a different effect on the components of the RAS. After the administration of a renin inhibitor, the formation of both Ang I and Ang II is blocked, thereby preventing the formation of angiotensin peptides by ACE and non-ACE pathways. These effects on the RAS provides the pharmacologic rationale for the study of renin inhibition in hypertension and cardiovascular diseases, and aliskiren (SPP100, SPP100A or SPP100B) is a potent and selective inhibitor of human renin: SPP100A (hydrochloride salt) demonstrated potent in vitro inhibition of human renin (IC50=0.6 nM).

In vivo, SPP100 administered both orally or intravenously in several studies with severely sodium-depleted marmoset monkeys caused complete inhibition of plasma renin activity, sustained reductions in mean arterial pressure and significant increases in plasma concentrations of active and total renin.

A dose ranging study of the effects of Aliskiren and losartan on ambulatory blood pressure monitoring of 4 weeks duration was conducted in patients with mild to moderate hypertension. Dose dependent decreases in blood pressure were observed in the dosage range of aliskiren 75 mg to 300 mg.

An open-label randomized pilot study was conducted comparing the effects of aliskiren versus ramipril on safety, tolerability, BNP (Brain Natriuretic Peptide) and RAAS (Renin Angiotensin Aldosteron System) hormones in patients with NYHA class II-IV heart failure and LVEF <35%. No deleterious effects on hormonal parameters were noted in either group. Trends towards reduced angiotensin II levels were observed in both aliskiren and ramipril groups. PRA was inhibited in the aliskiren group and increased in the ramipril group, in keeping with the different effects of renin and ACE inhibition on PRA.

The renin inhibitor aliskiren (INN name) is chemically 2(S),4(S),5(S),7(S)-N-(3-amino-2,2-dimethyl-3-oxopropyl)-2,7-di(1-methylethyl)4-hydroxy-5-amino-8-[4-methoxy-3-(3-methoxy-propoxy)phenyl]-octanamide of formula

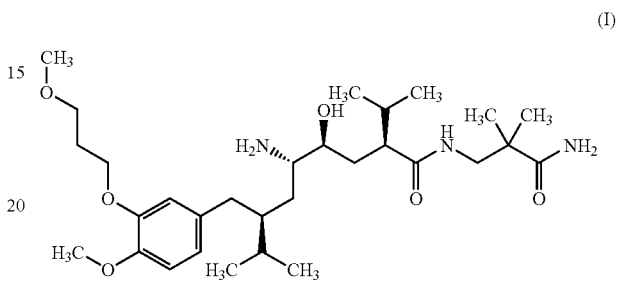

(I)

This compound and its manufacture are specifically disclosed in EP 678503 A.

The active ingredient aliskiren is the free base which is described specifically in EP 678503 A and it has one basic group, the amino group in position 5. This group has a pKa of 9.79 and can thus form salts with acids.

EP 678503 A, discloses the hydrochloride salt (example 137) and the hemifumarate salt (example 83) as specific salts of aliskiren. No crystalline forms are found there.

The oral administration of pharmaceutical agents such as aliskiren as tablets or capsules has certain advantages over parenteral administration such as i.v. or i.m. Diseases requiring treatment with painful injectable formulations are considered to be more serious than those conditions which can be treated with oral dosage forms. However, the major advantage with oral formulations is their suitability for self administration whereas parenteral formulations have to be administered in most cases by a physician or paramedical personnel.

Aliskiren hemifumarate is difficult to formulate. Typically, in a galenic formulation comprising aliskiren hemifumarate, a high amount is normally needed of the drug substance (DS) with properties that make the formulation of tablets difficult.

The drug substance quality is very variable with effect on the processability of a tablet, e.g., particle size distribution, bulk density, flowability, wetting behavior, surface area and sticking tendency. Aliskiren hemifumarate known so far is basically amorphous. Moreover, aliskiren is highly hygroscopic. The combination of these hurdles makes a standard tablet manufacturing process extremely difficult.

The low crystallinity, hygroscopicity and relatively low stability, in particular in the presence of moisture, leads to a more complicated manufacturing process in particular when isolating the final product. Specifically processes such as filtration and drying can be very long as a result of the above-mentioned less desirable properties of aliskiren hemifumarate. Aliskiren hemifumarate is also sensitive to the granulation process.

Therefore, despite the very major contribution which aliskiren has made, the reported undesirable properties have been an impediment with respect to the process economy.

Therefore, there is a need for more stable forms of aliskiren, which are even easier to manage in the drying, filtration or granulation processes following the final stage of the chemical preparation process and also in the steps for preparing the pharmaceutical formulations. Many futile attempts have been made to find improved forms through salt formation, the forms ideally being as crystalline as possible, as well as physically and chemically stable.

GENERAL AND DETAILED DESCRIPTION OF THE INVENTION

It has now surprisingly been possible to find novel crystal forms of aliskiren hemifumarate obtainable under rather specific conditions specified below. These crystal forms exhibit the desired improved properties.

Among the advantages of these crystalline materials, there are to be mentioned that these materials, due to their availability in crystalline form, allow for high purity products, make the handling of the material easier, allow for more stability of the bulk material and thus, for example, for easier and longer storing, and show other advantages, such as convenient dryability, better flowing characteristics, higher purity in view of the crystallinity, better definition of properties and the like.

The present invention therefore relates to novel crystal forms of aliskiren hemifumarate, processes for their manufacture, their use in the pharmaceutical field and pharmaceutical preparations comprising one or more of these crystal forms and/or aliskirene hemifumarate in different forms obtained during the manufacture of said pharmaceutical preparations, as well as processes for their manufacture and any related or other embodiments mentioned herein.

Figures: The figures (which also are part of the disclosure of specific embodiments of the invention) show the following (in parenthesis, parameters are shown in addition to those in the table before Example 1):

FIG. 1: X-ray powder diffraction pattern of Modification A (X-ray powder data measured with Scintag instrument with Cu K alpha radiation source; Step 0.020°, Cnt. time 2.400 sec., Range 2.00-40.00 (Deg.) Const. Scan Rate 0.50 Deg/min)

Figure 2:
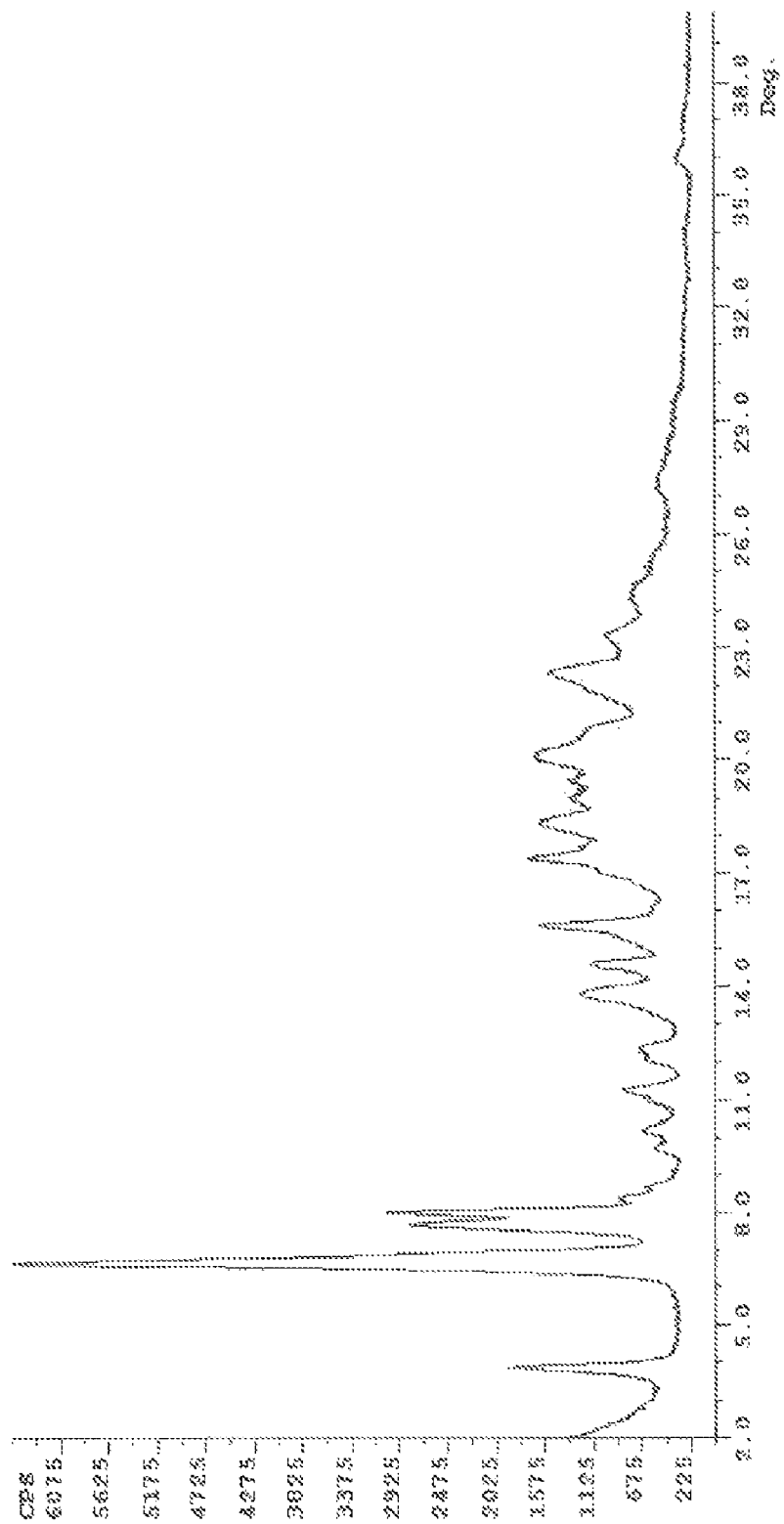

FIG. 2: X-ray powder diffraction pattern of Modification B (X-ray powder data measured with Scintag instrument with Cu K alpha radiation source; Step 0.020°, Cnt. time 2.400 sec., Range 2.00-40.00 (Deg.) Const. Scan Rate 0.50 Deg/min)

Figure 3:
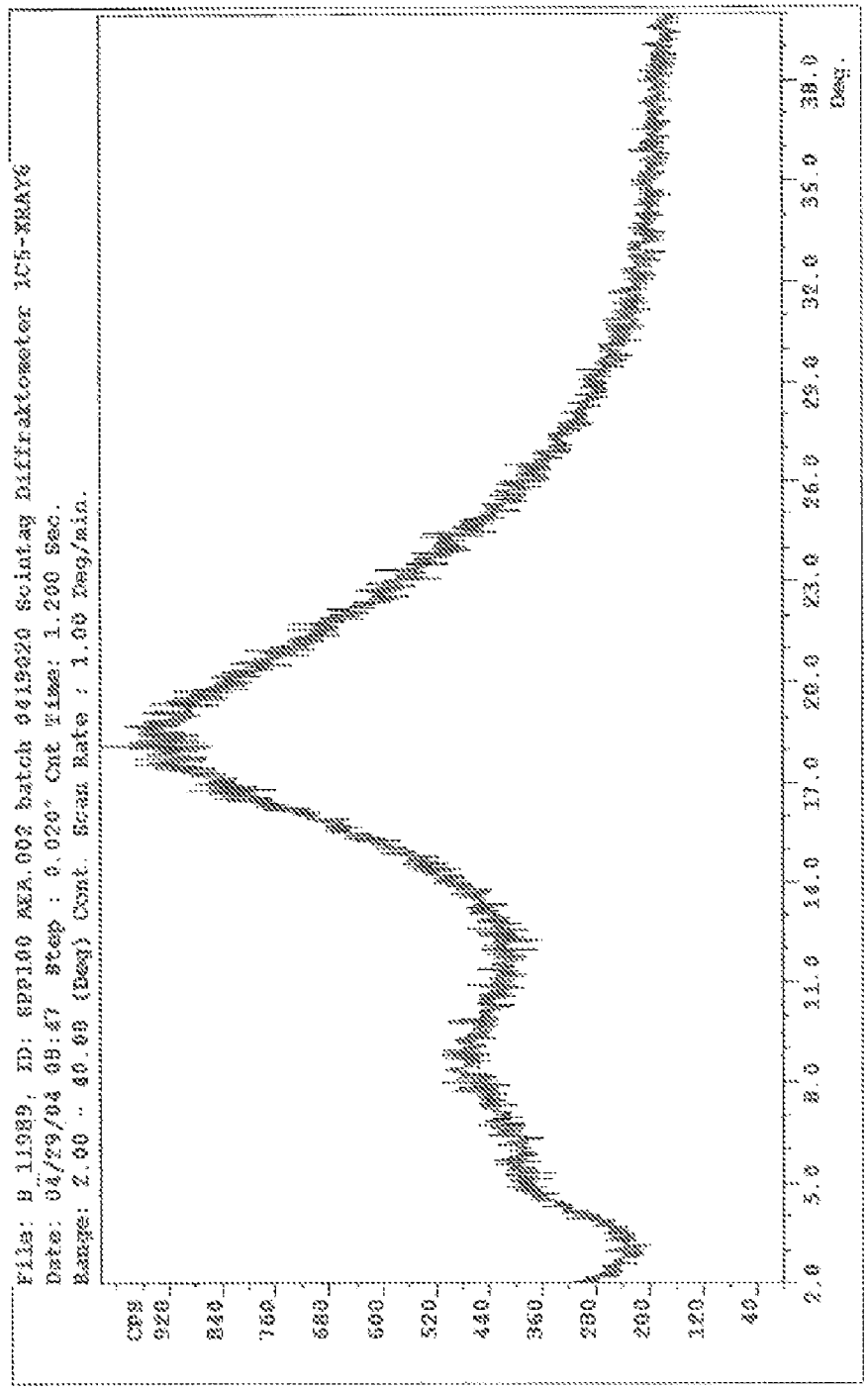

FIG. 3: X-ray powder diffraction pattern of amorphous aliskiren hemifumarate (X-ray powder data measured with Scintag instrument with Cu K alpha radiation source; Step 0.020°, Cnt. time 1.200 sec., Range 2.00-40.00 (Deg.) Const. Scan Rate 1.00 Deg/min).

Figure 4:
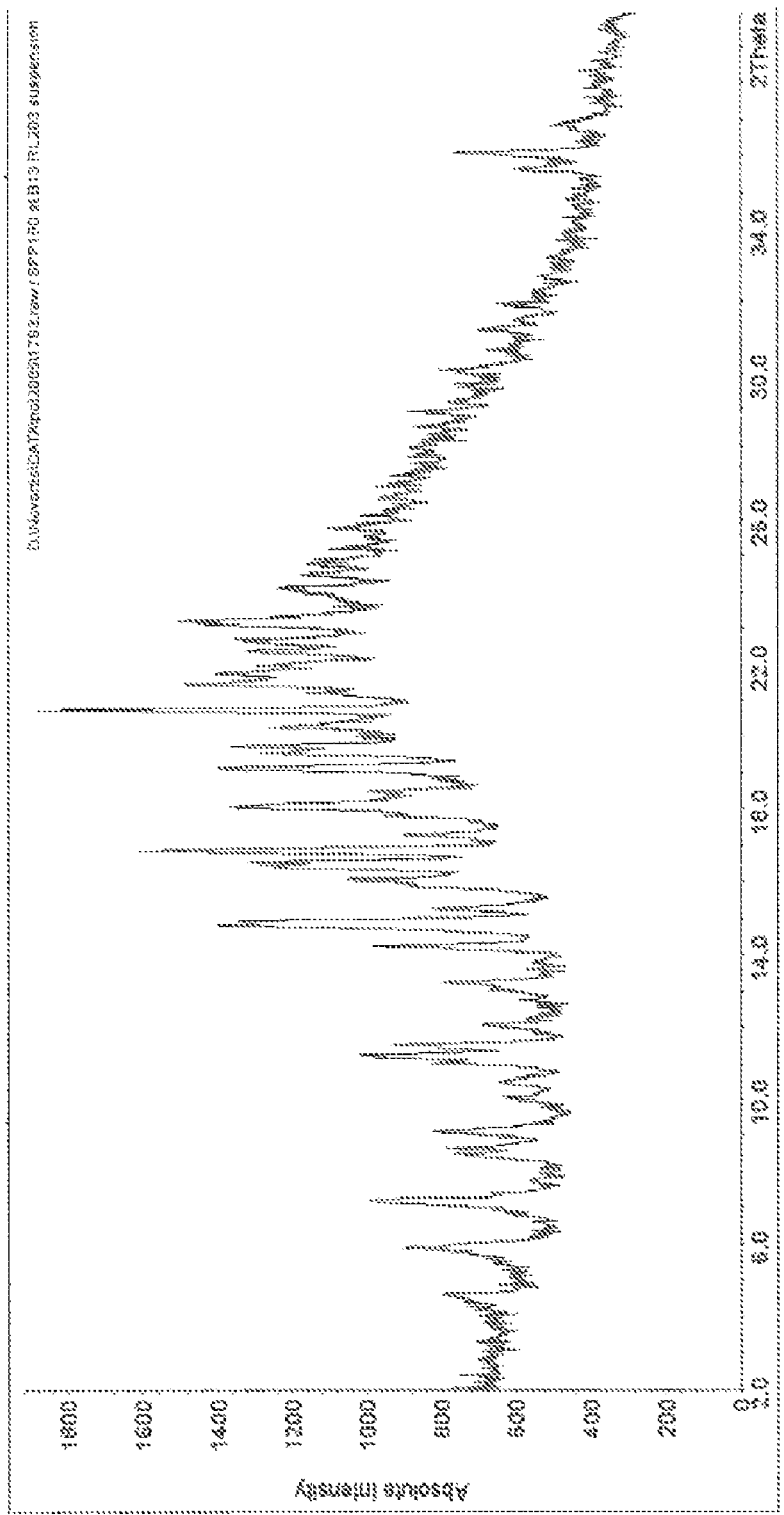

FIG. 4: X-ray powder diffraction pattern of Solvate Form $S_A$ (X-ray powder data measured with STOE Stadi P Combi instrument with Cu K alpha radiation source; Slit 4 mm/2 mm between kapton foil, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)=2.000, 39.980, 0.020; 325.0 sec/step, Imax=1884)

Figure 5:
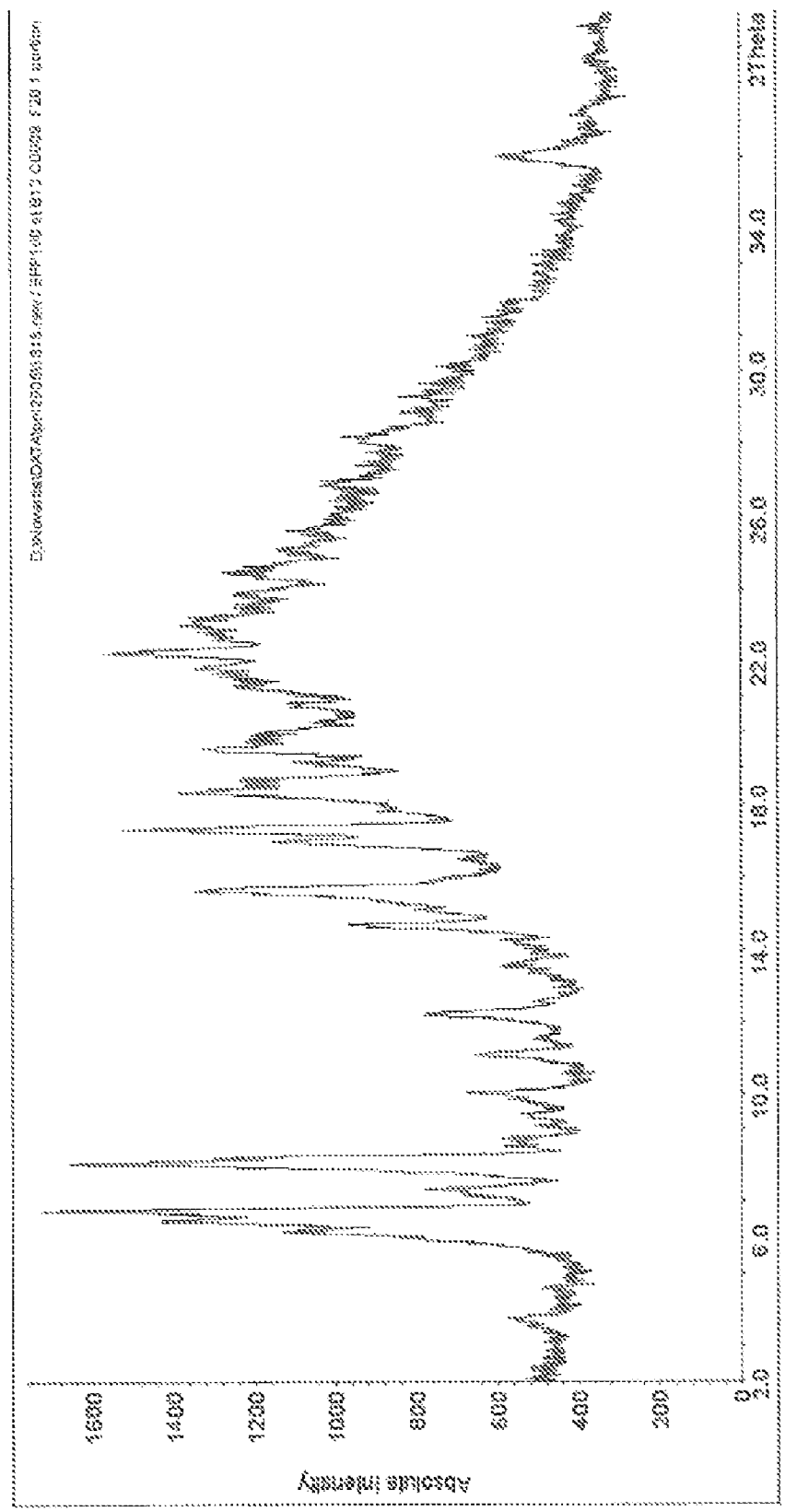

FIG. 5: X-ray powder diffraction pattern of Solvate Form $S_B$ (X-ray powder data measured with STOE Stadi P Combi instrument with Cu K alpha radiation source; Slit 4 mm/2 mm between kapton foil, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)=2.000, 39.980, 0.020; 260.0 set/step, Imax=1728)

Figure 6:
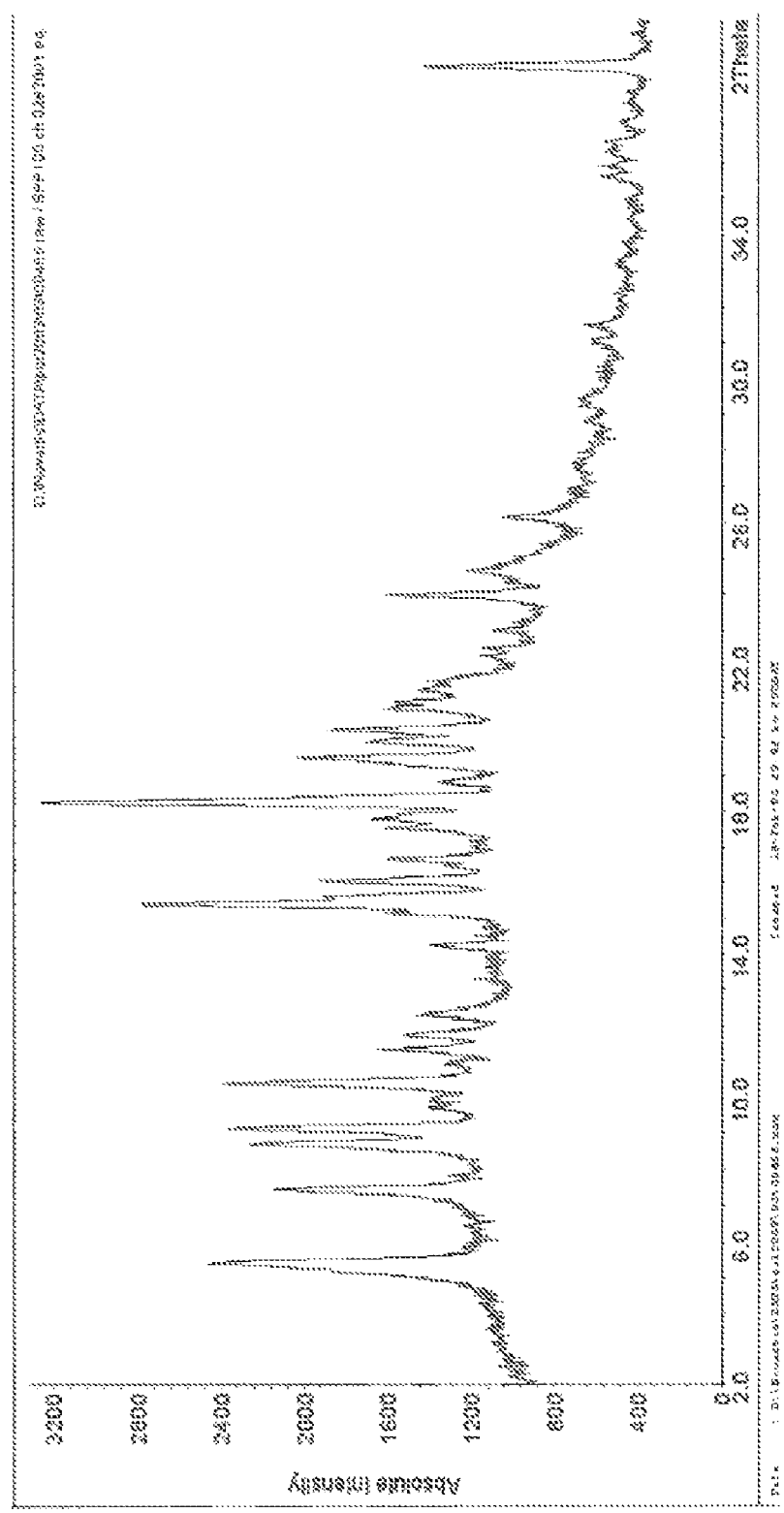

FIG. 6: X-ray powder diffraction pattern of Type III (Form A equilibrated in dioxane at 25° C.) (X-ray powder data measured with STOE Stadi P Combi instrument with Cu K alpha radiation source; Slit 4 mm/2 mm between kapton foil, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)=2.000, 39.980, 0.020; 390.00 sec/step, Imax=3259; Sample position 90.000, 45.000)

Figure 7:
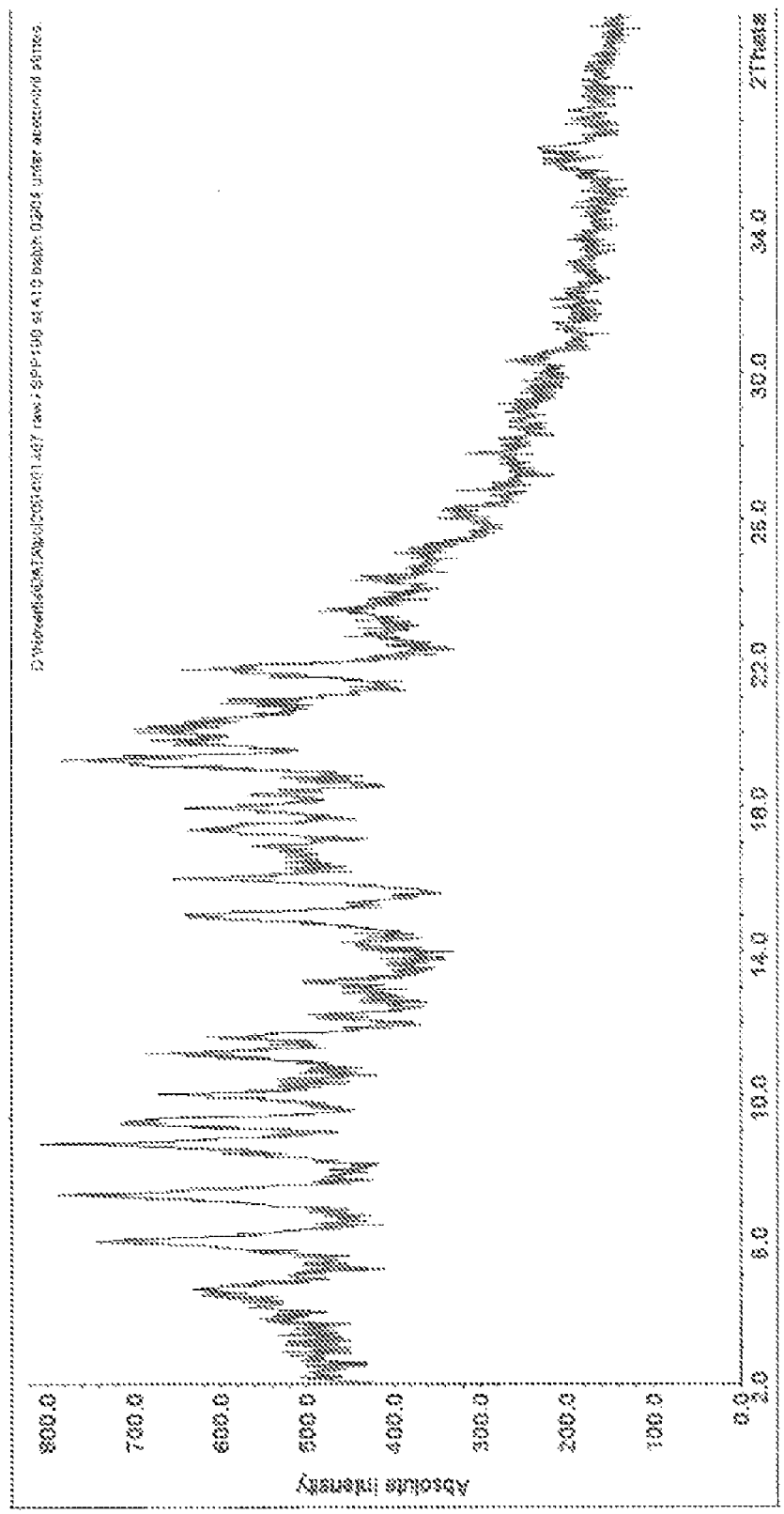

FIG. 7: X-ray powder diffraction pattern of Type IV (amorphous kept under acetonitrile atmosphere at 25° C.) (X-ray powder data measured with STOE Stadi P Combi instrument with Cu K alpha radiation source; Slit 4 mm/coll 2 mm between acetate foil ca. 15 mg, Transmission; Monochrom.: Curved Germanium (111), Radiation 1.54060 Cu, Generator: 50 kV, 30 mA, Detector: Linear PSD/Moving/Fixed Omega; Range 1: 2 Theta (begin, end, step)=2.000, 39.980, 0.020; 260.0 sec/step, Imax=808)

Figure 8:
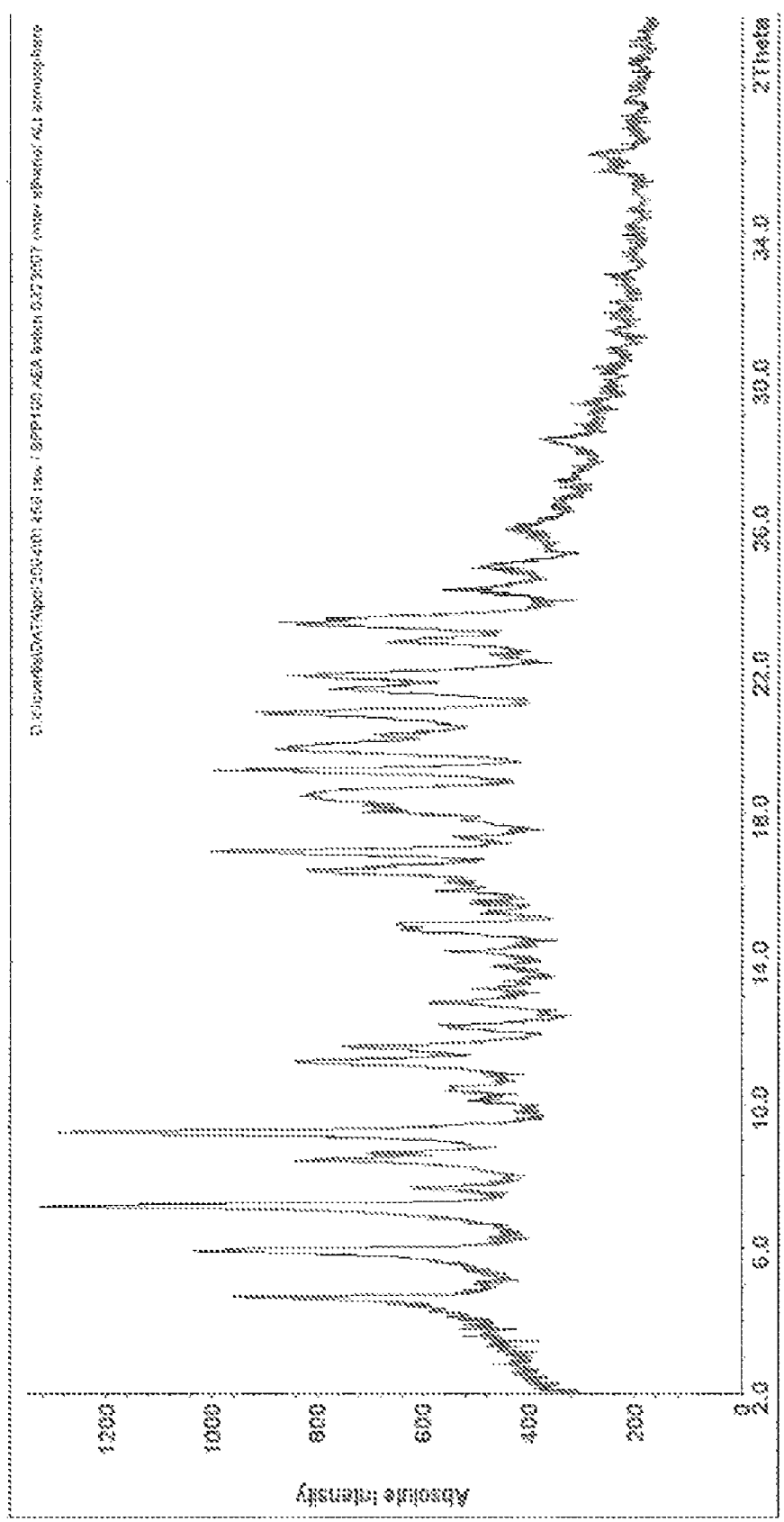

FIG. 8: X-ray powder diffraction pattern of Type VI (Form A kept under ethanol ALI (technical grade ethanol) atmosphere at 25° C. (X-ray powder data measured with STOE Stadi P Combi instrument with Cu K alpha radiation source; Slit 4 mm/coll 2 mm between acetate foil ca. 15 mg, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)= 2.000, 39.980, 0.020; 260.0 sec/step, Imax=1327)

Figure 9:
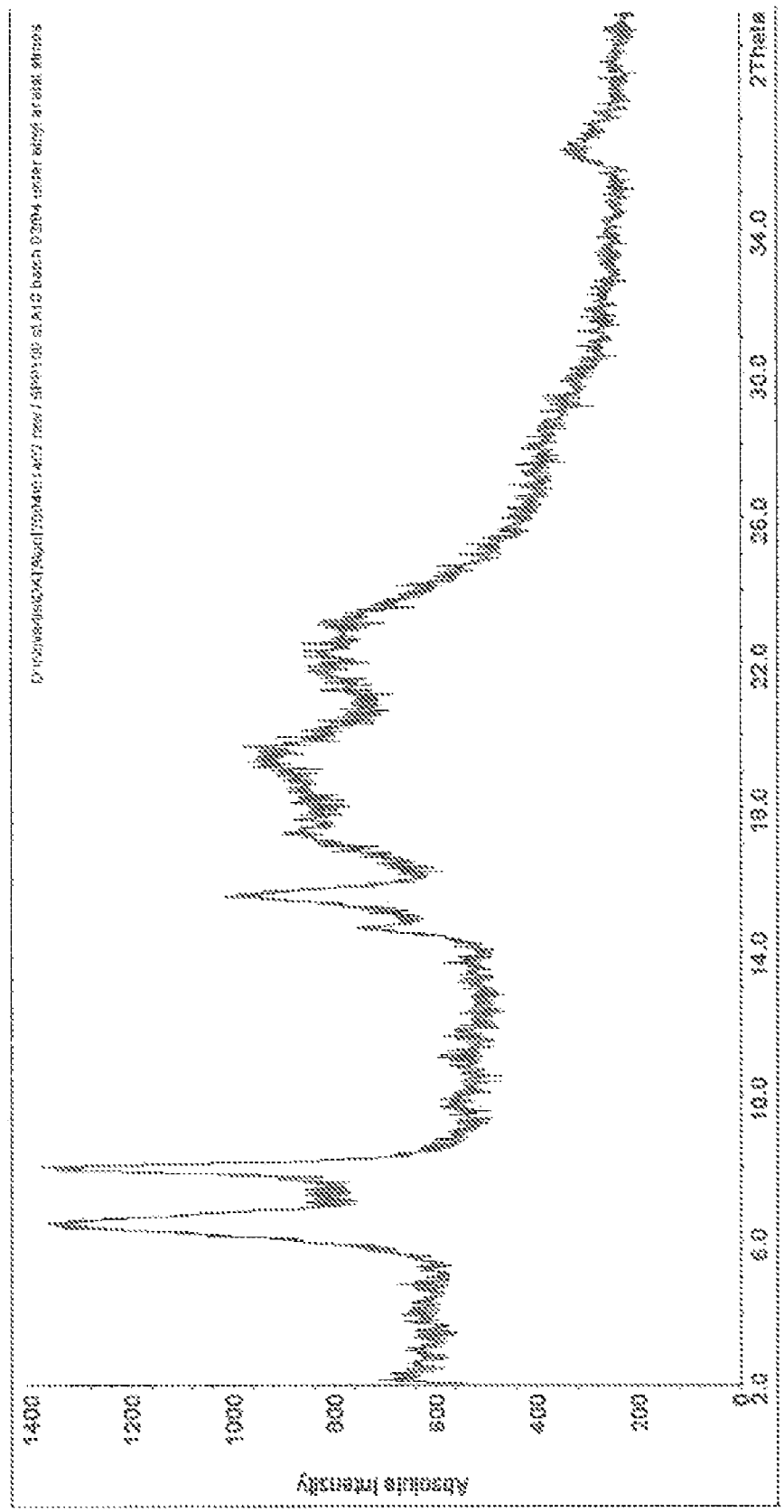

FIG. 9: X-ray powder diffraction pattern of Type I (amorphous kept under ethylacetate atmosphere at 25° C.) (X-ray powder data measured with STOE Stadi P Combi instrument with Cu K alpha radiation source; Slit 4 mm/coll 2 mm between acetate foil ca. 15 mg, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)=2.000, 39.980, 0.020; 260.0 sec/step, Imax=1381)

Figure 10:
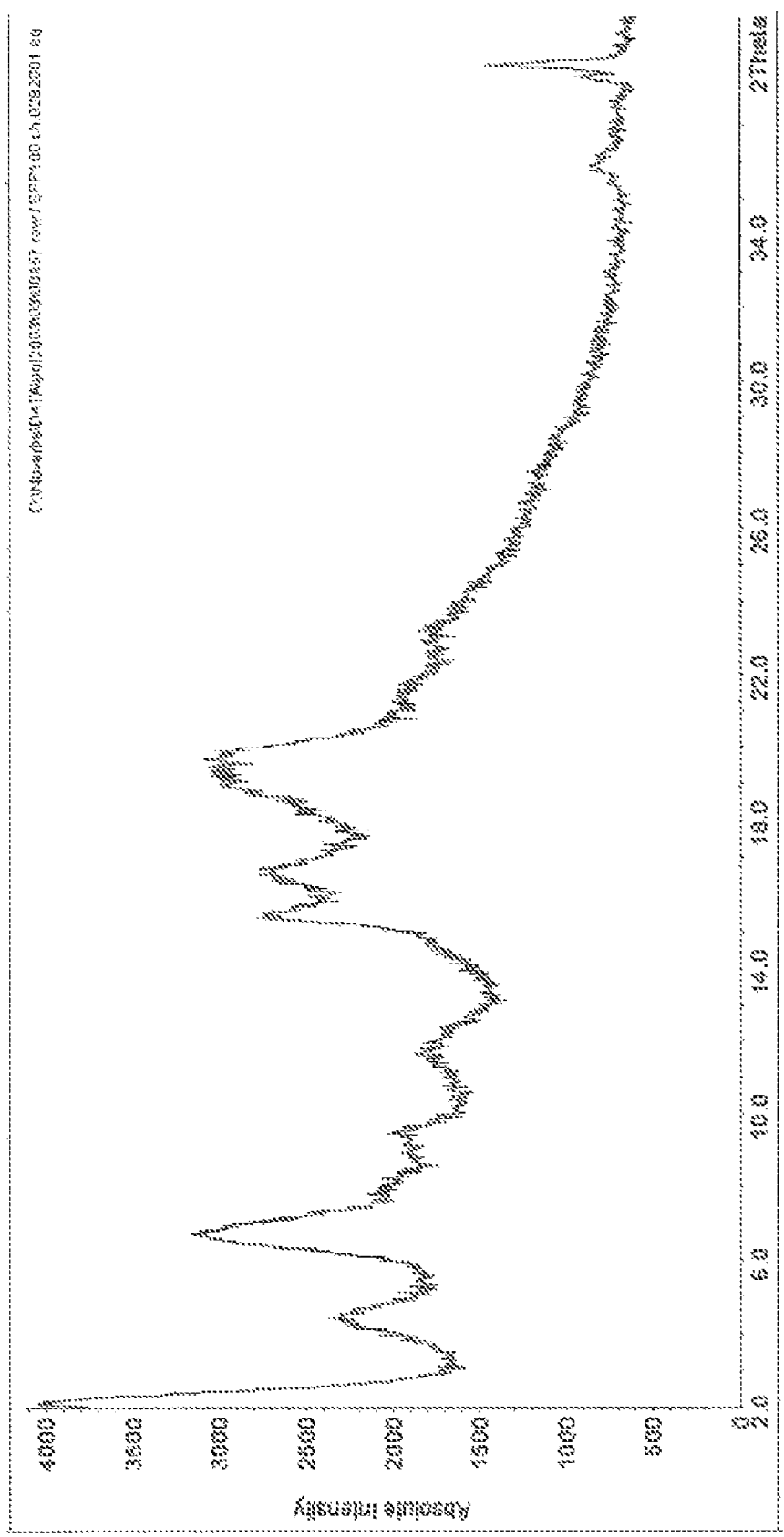

FIG. 10: X-ray powder diffraction pattern of Type II (Form A equilibrated in tert-butyl methylether at 25° C.) (X-ray powder data measured with STOE Stadi P Combi instrument with Cu K alpha radiation source; coll 2 mm slit, Sample position 10.000, 45.000, Transmission; Monochrom.: Curved Germanium (111), Radiation 1.54060 Cu, Generator: 50 kV, 30 mA, Detector: Linear PSD/Moving/Fixed Omega; Range 1: 2Theta (begin, end, step)=2.000, 39.980, 0.020; 390.0 sec/step, Imax=4043)

Figure 11:
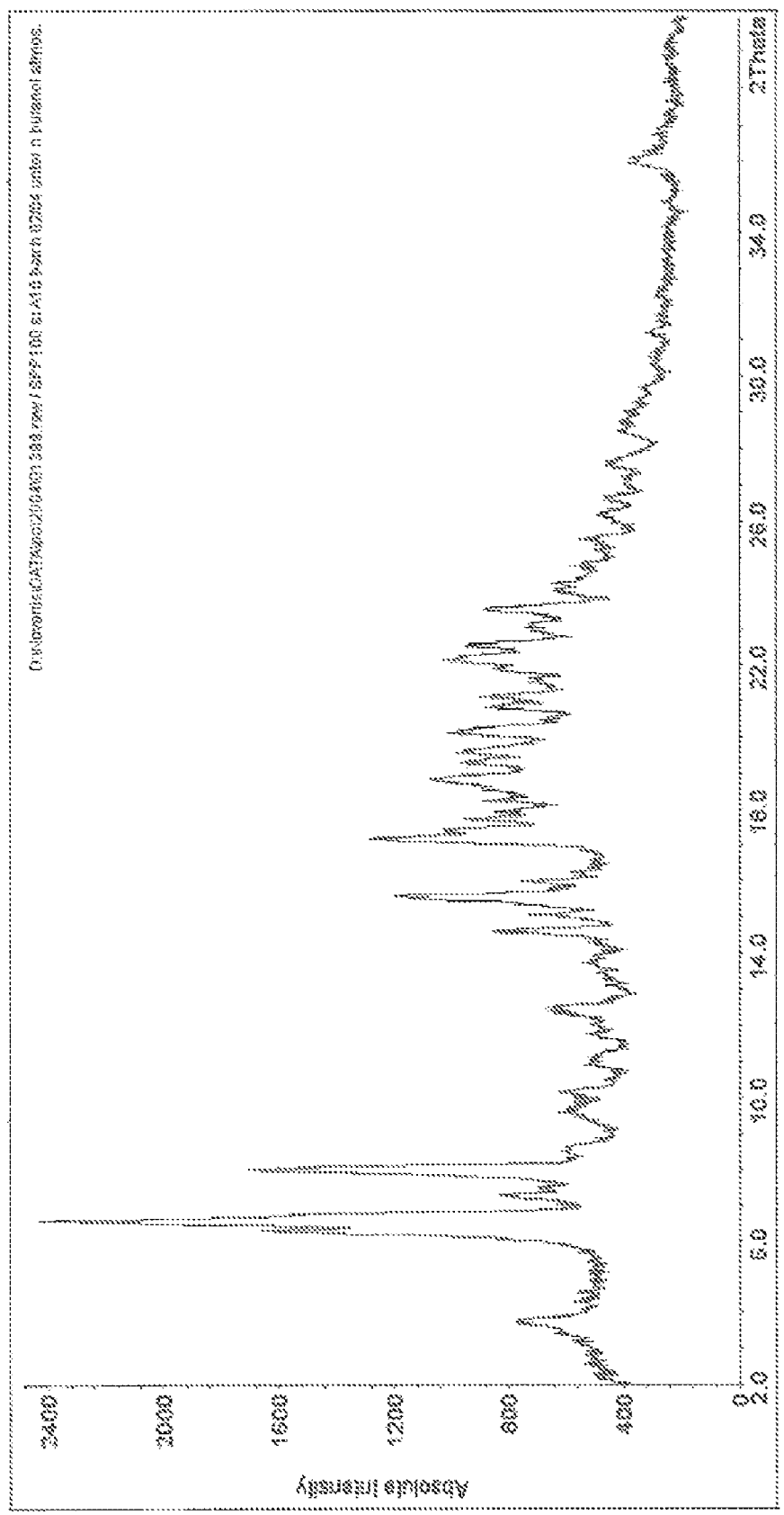

FIG. 11: X-ray powder diffraction pattern of Type V (amorphous kept under n-butanol atmosphere at 25 degree Celsius) (X-ray powder data measured with STOE Stadi P Combi instrument with Cu K alpha radiation source; Slit 4 mm/coll 2 mm between acetate foil ca. 15 mg, Transmission; Monochrom.: Curved Germanium (111), Radiation 1.54060 Cu, Generator: 50 kV, 30 mA, Detector: Linear PSD/Moving/ Fixed Omega; Range 1: 2Theta (begin, end, step)=2.000, 39.980, 0.020; 260.0 sec/step, Imax=2433).

Figure 12:
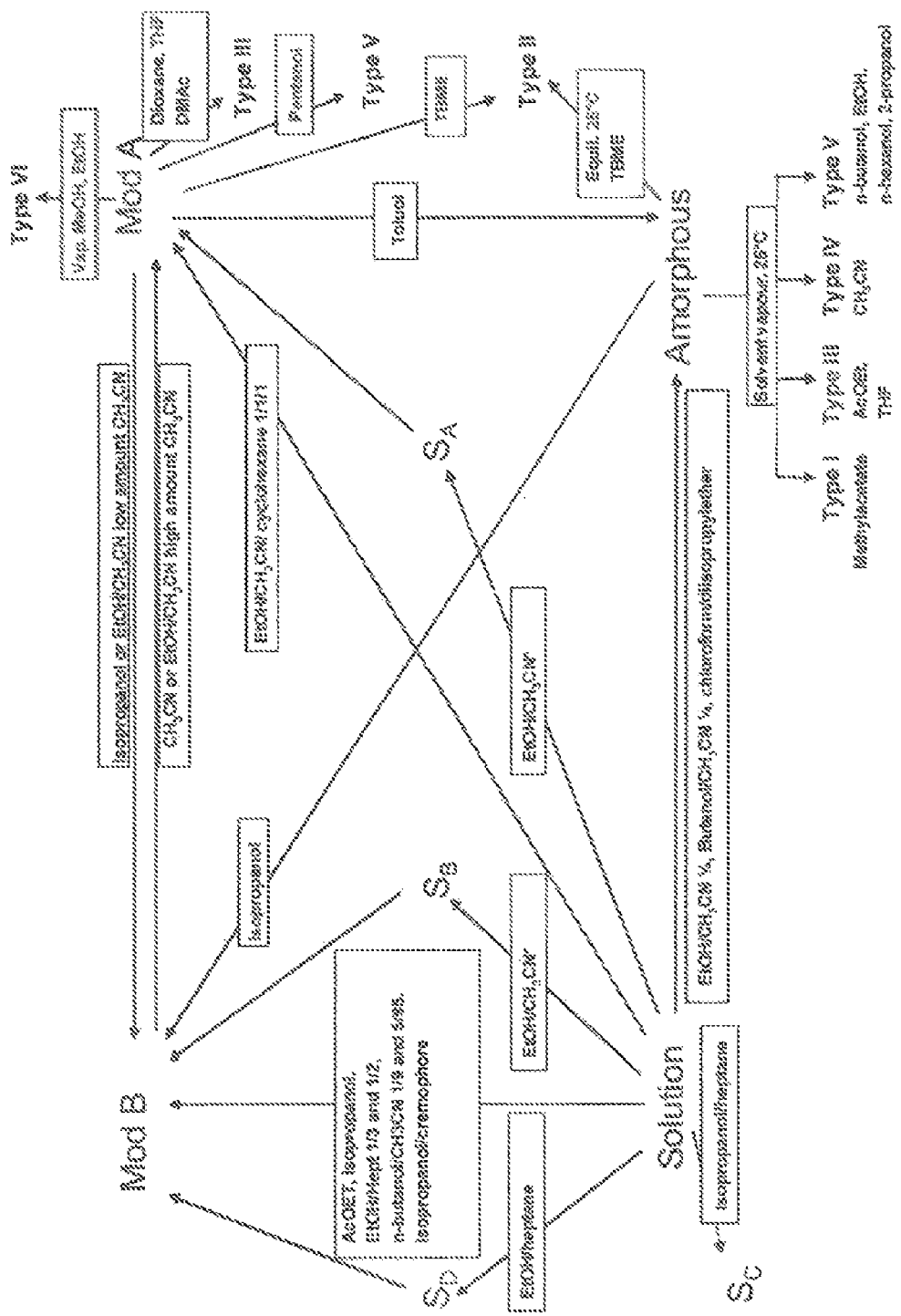

FIG. 12: Conversion scheme of different crystalline and the amorphous form of aliskiren hemifumarate (vap=vapour; toluol=toluene; DMAc=dimethylacetate; TBME=tert-butyl methylether; Hept=heptane).

The general terms used hereinbefore and hereinafter preferably have, within this disclosure, the following meanings, unless otherwise indicated (where preferred embodiments can be defined by replacing one or more up to all general expressions or symbols with (a) more specific or more preferred definition(s) given herein):

Where the plural form is used for compounds, salts, crystal forms, pharmaceutical compositions, diseases and the like, this is intended to mean also a single compound, salt, crystal form, pharmaceutical composition or the like.

The term "Crystal form" (or also Modification or, where solvents are present, solvate or solvate form) refers to a form of aliskeren hemifumarate (drug substance=DS) which comprises preferably at least 20%, more preferably at least 30%, yet more preferably at least 40%, especially 50% (by weight, respectively, and related to the total aliskirene hemifumarate present (=100%)) or more of a specific crystalline form of DS (especially besides other forms and/or preferably amorphous material). Among the specific crystalline forms, Modification B and in particular Modification A as described below in more detail are especially preferred. Further, this expression also relates to solvate forms, especially the forms $S_A$ (also called form E herein) and $S_B$ as well as $S_C$ (comprising isopropanol) and $S_D$ (comprising ethanol), Type I (comprising ethyl acetate), Type II (comprising tert-butylmethylether), Type III (comprising dioxane or tetrahydrofurane) (corresponding to Type D), Type IV (comprising acetonitrile), Type V (comprising pentanol, n-butanol, 2-propanol, 1-hexanol or ethanol) and Type VI (comprising ethanol or methanol), especially in the percentages just given. Note that, especially with regard to their X-ray diffraction patterns, types I, II and V are related to Modification A, types III, IV and VI to Modification B.

The term solvate includes hydrates; solvates mentioned specifically are preferred.

An overview of the relationship of the preferred different crystal forms according to the invention is represented by the conversion scheme given in FIG. 12.

Especially the bulk materials used for manufacture comprise a crystal form according to the invention, but also pharmaceutical preparations comprising the drug substance in crystalline form, especially with the percentages of crystalline form in relation to other (especially amorphous) forms of drug substance, given as preferred above and below, are preferred embodiments of the invention.

During the manufacture, at least part of the crystalline form may be lost, especially during wet granulation as described below (resulting e.g. in a part of the aliskiren hemifumarate present as amorphous material and/or solvate). Nevertheless, the easier handling, better storage stability etc. of the bulk material provide an advantage in the manufacture of pharmaceutical preparations also where such loss of crystallization occurs. Therefore, the manufacture of pharmaceutical formulations from such forms of the drug substance is also a preferred embodiment of the invention.

Where for the following preferred crystal forms according to the invention X-ray data are mentioned, they are preferably obtained under the conditions described in the corresponding figure legends.

The invention especially relates to a crystal form of aliskiren hemifumarate based on (=comprising at least 10%, preferably at least 20%, more preferably at least 30%, yet more preferably at least 40%, very preferably at least 50%, most preferably at least 60% (by weight, respectively) (e.g. in each case up to 90%, more preferably up to 95%), besides mainly amorphous material and possibly other crystalline forms of) a crystal form termed Modification A which has the following X-Ray diffraction pattern (under the conditions given in the description to FIG. 1) given as peaks at degrees 2Theta +/−0.3 degrees: 6.0. 7.3, 8.6, 9.2 and 9.9, more preferably at degrees 6.0, 7.3, 8.6, 9.2, 9.9, 15.0, 17.2 and 17.9, yet more preferably 6.0, 7.3, 8.6, 9.2, 9.9, 15.0, 17.2, 17.9, 19.2, 19.7, 20.1; especially an X-ray diffraction diagram corresponding to that given in FIG. 1.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal form termed Modification B which has the following X-Ray diffraction pattern (under the conditions given in the description to FIG. 2) given as peaks at degrees 2Theta +/−0.3 degrees: 3.8, 6.5, 7.7, 8.0, more preferably at degrees 3.8, 6.5, 7.7, 8.0, 15.6 and 17.4, yet more preferably 3.8, 6.5, 7.7, 8.0, 13.8, 14.5, 15.6, 17.4; especially an X-ray diffraction diagram corresponding to that given in FIG. 2.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Solvate Form $S_A$ which has the following X-Ray diffraction pattern given as peaks at degrees 2Theta +/−0.3 degrees: Peaks (°2Theta): 4.5, 5.9, 7.1, 14.8, 16.8, 18.0, 19.1 and 20.7, more preferably 4.5, 5.9, 7.1, 8.6, 9.1, 11.0, 11.2, 13.2, 14.2, 14.8, 15.2, 16.0, 16.4, 16.8, 18.0, 19.1, 19.7, 20.7, 21.4, 22.4, 22.6; especially an X-ray diffraction diagram corresponding to that given in FIG. 4.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Solvate Form $S_B$ which has the following X-Ray diffraction pattern (under the conditions given in the description to FIG. 5) given as peaks at degrees 2Theta +/−0.3 degrees: Peaks (°2Theta): 6.7, 7.2, 8.0, 12.2, 15.6, 16.9, 17.3 and 18.3, more preferably 3.7, 6.1, 6.4, 6.7, 7.2, 8.0, 10.0, 11.1, 12.2, 15.6, 16.9, 17.3, 18.3, 18.7, 19.5; especially an X-ray diffraction diagram corresponding to that given in FIG. 5.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type III, which has the following X-Ray diffraction pattern (under the conditions given in the description for FIG. 6) given as peaks at degrees 2Theta +/−0.3 degrees: Peaks (°2Theta): 5.4, 7.4, 8.7, 9.1, 10.3, 15.4, 16.0 and 18.2, more preferably 5.4, 7.4, 8.7, 9.1, 10.3, 11.3, 11.7, 12.3, 14.2, 15.1, 15.4, 16.0, 16.6, 17.8, 18.2, 19.4, 19.9, 20.2; especially an X-ray diffraction diagram corresponding to that given in FIG. 6.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type IV which has the following X-Ray diffraction pattern (under the conditions given in the description for FIG. 7) given as peaks at degrees 2Theta +/−0.3 degrees: Peaks (°2Theta): 4.5, 5.9, 7.2, 8.6, 9.2, 10.0, 11.1, 15.0 and 16.0, more preferably 4.5, 5.9, 7.2, 8.6, 9.2, 10.0, 11.1, 11.6, 15.0, 16.0, 17.4, 17.9, 19.2, 21.7; especially an X-ray diffraction diagram corresponding to that given in FIG. 7.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type VI, which has the following X-Ray diffraction pattern (under the conditions given in the description for FIG. 8) given as peaks at degrees 2Theta +/−0.3 degrees: Peaks (°2Theta): Peaks (°2Theta): 4.6, 5.9, 7.1, 9.2, 11.2, 14.8, 16.4, 16.9 and 19.2, more preferably 4.6, 5.9, 7.1, 8.4, 9.2, 11.2, 11.6, 12.1, 12.8, 14.8, 16.4, 16.9, 18.5,19.2, 19.8, 20.8, 21.4, 21.8, 23.3; especially an X-ray diffraction diagram corresponding to that given in FIG. 8.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type I which (under the conditions given in the description for FIG. 9) has the following X-Ray diffraction pattern given as peaks at degrees 2Theta +/−0.3 degrees: Peaks (°2Theta): 6.5, 8.0, 14.6, 15.5; especially an X-ray diffraction diagram corresponding to that given in FIG. 9.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type II which has the following X-Ray diffraction pattern (under the conditions given in the description for FIG. 10) given as peaks at degrees 2Theta +/−0.3 degrees: Peaks (°2Theta): 4.4, 6.7, 15.4 and 16.6, more preferably 4.4, 6.7, 9.4, 11.6, 15.4, 16.6, 19.7; especially an X-ray diffraction diagram corresponding to that given in FIG. 10.

In another embodiment, the invention relates to a crystal form of aliskiren hemifumarate based on (=comprising at least 10%, preferably at least 20%, more preferably at least 30%, yet more preferably at least 40%, very preferably at least 50%, highly preferably at least 80% and most preferably at least 90% (by weight, respectively), besides mainly amorphous material and possibly other crystalline forms of) a crystal solvate form termed Type V which has the following X-Ray diffraction pattern (under the conditions given in the description for FIG. 11) given as peaks at degrees 2Theta +/−0.3 degrees: Peaks (°2Theta): 3.7, 6.5, 8.0, 14.6, 15.5, 17.2, 18.8 and 20.1, more preferably 3.7, 6.3, 6.5, 7.2, 8.0, 9.6, 10.1, 12.4, 14.6, 15.1, 15.5, 17.2, 17.7, 18.8, 19.3, 19.6, 20.1, 22.1, 23.1; especially an X-ray diffraction diagram corresponding to that given in FIG. 11.

"An X-ray pattern corresponding" especially relates to one showing the same peaks, especially an about identical x-ray diagram under identical conditions as described for the respective example, e.g. in the figure descriptions and examples.

For the conditions for obtaining X-ray data (also in the Figures), in addition to the data given in the Figures see the "Table of methods and conditions used (if not mentioned otherwise)" before Example 1.

The X-ray diffraction pattern measurement instruments measure the diffracted x-ray intensity (counts per second, cps) with respect to the angle of the x-ray source. Only crystalline samples diffract at well defined angles, thus sharp peaks are observed depending on the nature of the crystal form. Each form will give a unique diffraction pattern. The intensity of the peaks depend on particle size and shape, thus it is a property of the batch not of the crystalline form. The diffraction peaks (pattern) defines the location of each atom within the molecule and defines the crystal symmetry and space group for the given crystal system.

It should be kept in mind that slight variations in observed 2Theta angles or d-spacing values are expected based on the specific diffractometer employed, the analyst, and the sample preparation technique. More variation is expected for the relative peak intensities.

Identification of the exact crystal form of a compound should be based primarily on observed 2Theta angles with no importance attributed to relative peak intensities.

Since some margin of error is possible in the assignment of 2Theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. Any 2Theta angles given may preferably differ within an interval of +/−0.3°, more preferably of +/−0.1°, from any 2Theta angle value given herein.

Any of the crystal forms mentioned above and below is advantageous, especially Modification B and most especially Modification A, both with regard to any embodiment of the inventtion, even though still amorphous material may be present within them, as they allow for more convenient purification, e.g. easier filtration, better separation from contaminations resulting from the chemical manufacture of the drug substance due to at least partial crystallization which results in more pure final material, better handling of the bulk material (e.g. easier pouring of the dry material, easier dosing, more stability, easier drying and the like), are very preferred.

Modification B is highly preferred as it can be obtained in highly pure form (with only low amounts of amorphous material, e.g. 10% or less, more preferably 5% or less present, where the % are weight percent and related to the total aliskirene hemifumarate present in the crystal form preparation).

Even more preferred is Modification A which, though it may be less pure with regard to accompanying amorphous material, does not form bundles of needle-like crystals as does Modification B, so that a possible disadvantage due to lower purity is more than compensated by the presence of crystals of a shape that is more convenient for production purposes both of the crystalline drug substance as well as pharmaceutical preparations comprising it.

The crystal forms can, in addition to the X-ray diffraction pattern, be further characterised by one or more of the corresponding properties given in the Examples, especially their way of manufacture (crystallization process), results from Differential Scanning Calorimetry, (especially the melting temperature ranges and/or melting enthalpies), lack of changes of the XRPD pattern on storage under nitrogen flow, X-Ray diffraction properties at various Relative Humidities, dynamic vapour sorption weight changes, heat of dissolution, equilibration behaviour in solvents, and/or other properties mentioned herein.

Especially preferred is a combination of one or more of these properties, especially the melting point (e.g. SPP100 hemifumarate melts within a range of about 95-104° C., especially 96 to 98° C. for Modification A, from 95 to 105° C., especially 99 to 102° C. for Modification B at a heating rate of 10 K/min, respectively) and the X-ray diffraction pattern. Still more preferred is a combination of the manufacturing method described in the Example and the X-Ray diffraction pattern from the tables, more preferably from the X-Ray diagrams depicted in the figures.

For both isopropanol solvate $S_C$ and ethanol solvate $S_D$, single crystals are obtained.

Here, also the parameters of the crystals depicted in Example 5 characterize a further preferred version of this solvate form, $S_D$.

The invention also relates to a process for the manufacture of a crystal form as described herein, as well as crystal forms obtainable (preferably obtained) by such a process.

Modifications A and B may be produced from solutions of aliskiren hemifumarate in ethanol with acetonitrile as antisolvent. A higher relative content of acetonitrile in comparison to the content of ethanol is in favour of yielding Modification A, a lower relative content is in favour of yielding modification B. In addition, the crystallization temperature is important: A higher temperature used during crystallization is in favour of yielding Modification A.

For example, Modification A can be obtained from a solution with a ratio by weight (w/w) of acetonitrile:ethanol in the range from 80:20 to 99:1, more preferably 85:15 to 90:10 (e.g. 87:13), at appropriate temperatures in the range from 15 to 40° C., e.g. (preferably after addition of seeding crystals of modification A e.g. at 37° C.) cooling down from 37° C. to 17° C. and re-warming to 37° C. and repeating the cooling and warming, and then cooling down to 22° C.; distilling off the solvent; adding acetonitrile, e.g. in a weight ratio aliskiren hemifumarate (amount used in the start) to acetonitrile of about 8:23, keeping at about 20° C., cooling to about 0 to 5° C., e.g. 3° C., filtration and washing (preferably with the mother liquor); followed by gentle drying.

More generally, Modification A can be obtained by gentle drying of Solvent form $S_A$.

Modification B can, for example, be obtained from a solution with a ratio by weight (w/w) of acetonitrile:ethanol in the range from 80:20 to 75:25 (e.g. 80:20) at appropriate temperatures in the range from 15 to 40° C., e.g. cooling down from 37° C. to 35° C. and (especially after a clouding occurs) further down to 20° C., allowing the aliskiren hemifumarate to crystallize, filtration and drying under vacuum, e.g. under 10 mbar at 40° C.

More generally, Modification B can be obtained from Solvent form $S_B$ by drying, e.g. under the conditions just described.

Modification B can also be obtained by slow solvent evaporation from ethylacetate or isopropanol, e.g. by dissolving aliskiren hemifumarate in the solvent at about 20° C. and then slowly evaporating at room temperature.

Solvent form $S_A$ can, for example, be obtained as described above for the manufacture of Modification A, however, omitting the filtration and the drying.

Solvent Form $S_B$ can, for example, be obtained as described above for Modification B, however, omitting the filtration and drying step.

Solvent Form $S_C$ can be obtained from an isopropanol solution of aliskiren hemifumarate by precipitation using heptane as antisolvent.

Solvent Form $S_D$, can be obtained from an ethanol solution of aliskiren hemifumarate by precipitation using heptane as antisolvent.

Solvent Form Type I can be obtained by crystallization from amorphous material by keeping it under an ethylacetate and/or methylacetate atmosphere.

Solvent Form Type II can be obtained from Modification A and/or from amorphous aliskiren hemifumarate by keeping it under a tert-butyl methyl ether atmosphere.

Solvent Form Type III (corresponding to solvent Form $S_D$) can be obtained from Modification A by keeping it under a dioxane, tetrahydrofurane and/or ethyl acetate atmosphere.

Solvent Form Type IV can be obtained from amorphous aliskiren hemifumarate by keeping it under acetonitrile atmosphere.

Solvent Form V can be obtained from Modification A by keeping it under a pentanol atmosphere and/or from amorphous aliskiren hemifumarate by keeping it under a n-butanol, 2-propanol, 1-hexanol or ethanol atmosphere.

Solvent Form Type VI can be obtained from Modification A by keeping it under ethanol and/or methanol atmosphere.

These and other conditions for obtaining the crystal forms according to the invention can also be deduced from the Examples as well as from FIG. 12.

No change of the crystalline Modification A, Modification B and amorphous aliskiren hemifumarate is observed in cyclohexane or n-heptane.

Amorphous material can e.g. be obtained by spray drying under customary conditions, e.g. from an ethanol solution, preferably followed by further drying the obtained material e.g. at 20 mBar and 30° C.

Where the term "comprising" is used, this is intended to mean that the component, components, action, actions, feature or features mentioned or enumerated thereafter may be fulfilled not only alone, but that also one or more other components and/or features (e.g. other additives, other actions) may be present in addition to those specifically mentioned. This is in contrast to the term "containing" or "consisting of" which here mean that no other components or features are included except for those specifically mentioned after such an expression and thus denote a complete enumeration/representation of features and/or components. Whereever "comprising" is used, this may (independently of other occurrences) be replaced by the narrower term "consisting of" or (in case of processes or methods) by "containing the step of", where possible and expedient, thus leading to specific and preferred embodiments of the invention.

The amorphous state generally is a disordered solid state, which may e.g. appear during manufacture of the drug substance (crystallization step, drying, milling) or the drug product (granulation, compression).

"A form obtainable therefrom during the manufacturing process of a corresponding pharmaceutical preparation" ("obtainable" wherever mentioned especially meaning "obtained") preferably means that where, during the manufacturing process, the crystal form may be transformed and/or (at least partially) removed from the original crystal form (e.g. during wet granulation procedures), other forms (e.g. amorphous and/or solvate forms or the like) may form and may be present in the final pharmaceutical formulation instead of all or preferably only part of the original crystal form. Preferably both the crystal form (e.g. in the percentages given as preferred above) and forms obtainable therefrom (e.g. the amorphous or solvate forms) are present simultaneously. Where a crystal form is mentioned with regard to treatment, preparations or the like, this preferably includes "a crystal form and a form obtainable therefrom during the manufacturing process of a corresponding pharmaceutical preparation".

The crystal forms (preferably one of them, especially Modification A) according to the inventtion, or, or preferably and, a form obtainable (especially obtained) therefrom during the manufacturing process of a corresponding pharmaceutical preparation, may be used e.g. in the form of pharmaceutical preparations, which comprise the active ingredient especially in a therapeutically effective amount of the active substance, optionally together with a pharmaceutically acceptable carrier, for example with an inorganic or organic, solid or optionally also liquid pharmaceutically acceptable carrier, which is suitable for enteral, e.g. oral, or parenteral administration.

The invention relates in particular to a pharmaceutical composition, especially in a solid dosage unit, preferably for oral administration, optionally together with a pharmaceutically acceptable carrier, obtainable from using a crystal form according to the invention as active ingredient.

Pharmaceutical preparations of this kind may be used for example for the prophylaxis and treatment of diseases or conditions which may be treated or modulated, especially inhibited, by blocking the $AT_1$ receptor, for example a disease or condition selected from the group consisting of
(a) hypertension, whether of the malignant, essential, renovascular, diabetic nephropathy, diabetic cardiac myopathy, isolated systolic, or other secondary type; congestive heart failure, renal insufficiency or failure, especially chronic renal failure, restenosis after percutaneous transluminal angioplasty, and restenosis after coronary artery bypass surgery;
(b) atherosclerosis, nephropathy, renal failure, e.g. chronic renal failure, hypothyroidism, myocardial infarction, especially survival post myocardial infarction (MI), coronary heart diseases, e.g. angina (whether unstable or stable), hypertension in the elderly, familial dyslipidemic hypertension, increase of formation of collagen, fibrosis, and remodeling following hypertension (antiproliferative effect of the combination), all these diseases or conditions associated with or without hypertension;
(c) endothelial dysfunction with or without hypertension, or peripheral vascular disease,
(d) hyperlipidemia, hyperlipoproteinemia, atherosclerosis and hypercholesterolemia,
(e) glaucoma,
(f) Diabetes Type II (insulin resistance)
(g) Metabolic Syndrome (also called Syndrome X; present if at least three of the following criteria are met: 1) abdominal girth of men>102 cm/of women>88 cm; 2) Fasting Plasma HDL-C (High Density Lipid Cholesterol)<40 mg/dl in men,<50 mg/ml in women; 3) fasting plasma triglyceride>150 mg/dl; 4) blood pressure>130/85 mm Hg; and 5) impaired glucose regulation/insulin resistance=fasting plasma glucose equal or higher than 100 mg/dl (see J. Am. Med. Assoc. 285(3), 2486-97 (1991)),
(h) diseases resulting from the conditions mentioned under (f) and/or (g), such as inflamemation, high blood pressure, high triglyceride level, visceral adiposity, obesity in general, prothrombotic state (including e.g. impaired fibrinolysis and/or procoagulation), low HDL-C level, high blood glucose level, especially glucose intolerance, neuropathy, retinopathy, nephropathy, cardiovascular disorders and diabetes, and
(i) left ventricular hypertrophy, cognitive dysfunction, e.g., Alzheimer's, stroke, headache and chronic heart failure.

The present invention therefore also relates to the use of a crystal form (as such or in the form of a pharmaceutical preparation or, or preferably and, as a form obtainable (especially obtained) therefrom during the manufacturing process of a corresponding pharmaceutical preparation" according to the invention) for the prophylaxis and/or treatment of any one or more of the diseases mentioned above, to the use of use of a crystal form (as such or in the form of a pharmaceutical preparation or, or preferably and, as a form obtainable (especially obtained) therefrom during the manufacturing process of a corresponding pharmaceutical preparation according to the invention) in the manufacture of a pharmaceutical preparation that can be (preferably is) used in the prophylaxis and/or treatment of any one or more of the diseases mentioned above, to a method of treatment of a warm-blooded animal in need of such treatment, especially a human in need of such treatment, comprising administering a crystal form according to the invention or a pharmaceutical preparation comprising a crystal form or, or preferably and, a form obtainable (especially obtained) therefrom during the manufacturing process of a corresponding pharmaceutical preparation according to the invention) in an amount effective for the prophylaxis and/or treatment of said disease, as well as a pharmaceutical preparation, comprising a crystal form according to the invention or use of a crystal form (or, or preferably and, a form obtainable therefrom during the manufacturing process of a corresponding pharmaceutical preparation) and at least one pharmaceutically acceptable carrier material.

Primary usages are for the treatment of high blood pressure and congestive heart failure, as well as post-myocardial infarction.

The efficiency of the crystal forms of aliskiren according to the invention can be readily identified e.g. by the test systems identified in EP 0 678 503 A1 which, in this regard, is incorporated by reference herewith. For example, the in vitro determination of renin inhibitory activity is possible using different assay systems, e.g. human plasma, purified human renin together with synthetic or natural renin substrate, respectively. One possible test system is as follows: An extract of human renin from kidney (isolated or obtained recombinantly) (0.5 mGU (=Milli-Goldblatt-Units)/ml) is incubated for one hour at 37° C. and pH 7.2 in 1-molar aqueous 2-N-(tris-hydroxymethylmethyl)-amino-ethansulfonic acid buffer solution with 23 µg/ml synthetic renin substrate, the decapeptide H-Asp-Arg-Val-Tyr-Ile-His-Pro-Phe-His-Leu-Leu-Val-Tyr-Ser-OH. The amount of Angiotensin I formed is determined by radioimmuno assay. Crystal form with aliskiren as the active principle activity are added each in different concentrations. The concentration of the respective compound at which the formation of Angiotensin II is diminished by 50% is called the $IC_{50}$. Preclinical and clinical studies confirm the efficacy in vivo.

The person skilled in the pertinent art is fully enabled to select a relevant and standard animal test model to prove the hereinbefore and hereinafter indicated therapeutic indications and beneficial effects, and/or to conduct the corresponding clinical trials.

The present pharmaceutical preparations which, if so desired, may apart from a crystal form according to the invention and/or a form of aliskirene hemifumarate obtained during the manufacture of the corresponding pharmaceutical preparation from such a crystal form, in the case of combination products, comprise further pharmacologically active substances, are prepared in a manner known per se, for example by means of conventional mixing, granulating, coating, dissolving or lyophilising processes, and comprise preferably from about 0.1% to 100%, especially from about 1% to about 50%, in case of lyophilisates up to 100% of the active substance (here aliskiren hemifumarate) or, in the case of combination, active substances.

The invention similarly relates to compositions comprising a crystal form according to the inventtion, preferably aliskiren hemifumarate with at least 10%, more preferably at least 20%, yet more preferably at least 30%, highly preferably at least 40% and most preferably at least 50% proportion of a crystal form according to the invention, especially Modification A and/or a solvate thereof (with the percentages given in weight percent, related to the total amount of aliskiren hemifumarate present which is 100%).

The invention similarly relates to the use of a crystal form according to the invention preferably for the production of pharmaceutical preparations, especially for the prophylaxis and also for the treatment of diseases or conditions which may be modulated by renin inhibition. Primary usages are for the treatment of high blood pressure, renal failure, left ventricular dysfunction and heart failure.

The invention similarly relates to the use of a crystal form according to the invention, and/or, preferably and, a form obtainable (especially obtained) therefrom during the manufacturing process of a corresponding pharmaceutical preparation, for the prophylaxis and treatment of diseases or conditions which may be modulated by renin inhibition, characterised in that a patient, including a human patient, requiring such treatment is administered with a therapeutically effecttive amount of crystal form according to the invention, and/or, preferably and, a form obtainable (especially obtained) therefrom during the manufacturing process of a corresponding pharmaceutical preparation, optionally in combination with at least one further active substance for the treatment of cardiovascular diseases and related conditions and diseases listed hereinbefore or hereinafter.

The invention similarly relates to combinations, e.g. pharmaceutical combinations, containing a crystal form of the present invention, and/or, preferably and, a form obtainable (especially obtained) therefrom during the manufacturing process of a corresponding pharmaceutical preparation, in combination with one or more further active ingredients, or pharmaceutically acceptable salts thereof, especially for the treatment of cardiovascular diseases and related conditions and diseases as listed hereinbefore or hereinafter. Combinations with other compositions for the treatment of cardiovascular diseases and related conditions and diseases as listed hereinbefore or hereinafter, or in each case a pharmaceutically acceptable salt thereof, are likewise objects of the present invention.

The combination may be made for example with the following compositions, selected from the group consisting of a:
(i) HMG-Co-A reductase inhibitor or a pharmaceutically acceptable salt thereof,
(ii) angiotensin converting enzyme (ACE) Inhibitor or a pharmaceutically acceptable salt thereof,
(iii) calcium channel blocker (CCB) or a pharmaceutically acceptable salt thereof,
(iv) aldosterone synthase inhibitor or a pharmaceutically acceptable salt thereof,
(v) aldosterone antagonist or a pharmaceutically acceptable salt thereof,
(vi) dual angiotensin converting enzyme/neutral endopeptidase (ACE/NEP) inhibitor or a pharmaceutically acceptable salt thereof,
(vii) endothelin antagonist or a pharmaceutically acceptable salt thereof,
(viii) angiotensin II receptor blockers (ARB) or a pharmaceutically acceptable salt thereof, and
(ix) diuretic or a pharmaceutically acceptable salt thereof.

HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting or alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or a pharmaceutically acceptable salt thereof, respectively.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs. Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)–enantiomer thereof), as well as the steroidal aromatase inhibitor exemestane, or, in each case where applicable, a pharmaceutically acceptable salt thereof.

The most preferred non-steroidal aldosterone synthase inhibitor is the (+)–enantiomer of the hydrochloride of fadrozole (U.S. Pat. Nos. 4,617,307 and 4,889,861).

A preferred steroidal aldosterone antagonist is eplerenone or spironolactone.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

Suitable angiotensin II receptor blockers which may be employed in the combination of the present invention include $AT_1$-receptor antagonists having differing structural features, preferred are those with the non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-4177 of the formula

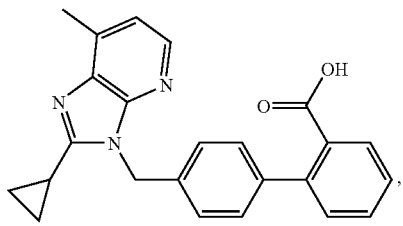

the compound with the designation SC-52458 of the following formula

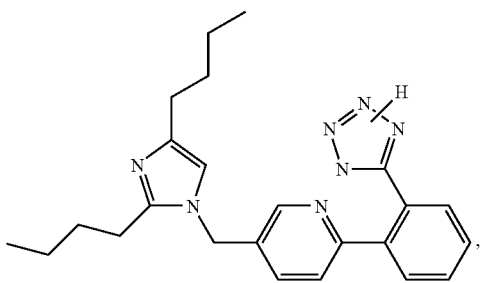

and the compound with the designation the compound ZD-8731 of the formula

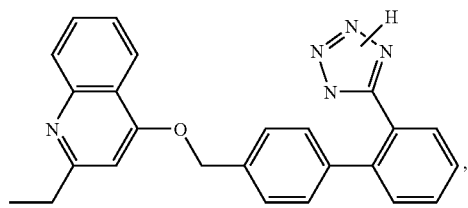

or, in each case, a pharmaceutically acceptable salt thereof.

Preferred $AT_1$-receptor antagonists are those agents that have reached the market, most preferred is valsartan, or a pharmaceutically acceptable salt thereof.

A diuretic is, for example, a thiazide derivative selected from the group consisting of chlorothiazide, methylclothiazide, chlorothalidon and especially hydrochlorothiazide.

Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or pharmaceutically acceptable salts thereof may also be used in form of a solvate, such as a hydrate or including other solvents, used for precipitation or crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

In a variation thereof, the present invention likewise relates to pharmaceutical product in the form of a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The invention furthermore relates to a commercial package (pharmaceutical product) comprising the combination according to the present invention together with instructions for simultaneous, separate or sequential use.

Dosaging of the crystal forms according to the invention and/or, preferably and, a form obtainable (especially obtained) therefrom during the manufacturing process of a corresponding pharmaceutical preparation, may depend on various factors, such as mode of application, species, age and/or individual condition. For example, the doses to be administered to warm-blooded animals, including man, of approximately 75 kg body weight, especially the doses effective for the inhibition of renin activity, e.g., in lowering blood pressure, are from about 3 mg to about 3 g, preferably from about 10 mg to about 1 g, e.g., from 20 to 600 mg/person/day, bases on the free base of aliskiren, respectively, divided preferably into 1 to 4 single doses which may, e.g., be of the same size. Usually, children receive about half of the adult dose. The dose necessary for each individual can be monitored, e.g., by measuring the serum concentration of the active ingredient, and adjusted to an optimum level.

Single doses comprise, e.g., 75 mg, 150 mg or 300 mg per adult patient based on the free base of aliskiren.

The present invention also relates to a pharmaceutical preparation comprising a crystal form according to the invention, and/or, preferably and, a form obtainable (especially obtained) therefrom during the manufacturing process of a corresponding pharmaceutical preparation, and one or more pharmaceutically acceptable carrier materials, especially useful in a process suitable for large-scale manufacture of solid oral dosage forms.

The present invention thus especially relates to a solid oral dosage form comprising a therapeutically effecttive amount of a crystal form according to the invention, wherein the active ingredient (calculated as aliskiren free base) is present in an amount of more than 46% by weight based on the total weight of the oral dosage form, either dependent on or not dependent on any coating or capsule material used.

If not dependent on any coating or capsule used, the active ingredient is present in an amount of more than 48% by weight based on the total weight of the oral dosage form. If dependent on any coating or capsule used, the active ingredient is present in an amount of more than 46% by weight based on the total weight of the oral dosage form.

In a preferred embodiment of the present invention, the active ingredient is present in an amount ranging from 46 to 60% by weight based on the total weight of the oral dosage form.

In another preferred embodiment of the present invention, the active agent is present in an amount of more than 46% up to 56% by weight based on the total weight of the oral dosage form.

In a solid oral dosage form according to the present invention wherein the active agent consists entirely of a crystal form according to the invention and/or, preferably and, a form obtainable (especially obtained) therefrom during the manufacturing process of a correspondding pharmaceutical preparation, it is preferred if this active ingredient is present in an amount ranging from about 75 mg to about 600 (preferably to about 300) mg of the free base per unit dosage form.

In a further preferred embodiment of the present invention, the dosage is present in an amount of about 83, about 166, about 332 or about 663 mg per unit dosage form, based on the aliskiren hemifumarate salt.

Preferred solid oral dosage forms according to the present invention provide for the administration of the active ingredient in a smaller oral form than was heretofore possible for a given unit dose of the active agent. Furthermore, the oral dosage forms obtained are stable both to the production process and during storage, e.g., for about 2 years in conventional packaging, e.g., sealed aluminium blister packs.

The terms "effective amount" or "therapeutically effective amount" refers to the amount of the active ingredient or agent which halts or reduces the progress of the condition being treated or which otherwise completely or partly cures or acts otherwise in an improving manner on the condition.

A solid oral dosage form comprises a capsule or more preferably a tablet or a film-coated tablet.

A solid oral dosage form according to the invention comprises pharmaceutically acceptable carrier materials, e.g. additives or excipients that are suitable for the preparation of the solid oral dosage form according to the present invention. Tabletting aids, commonly used in tablet formulation can be used and reference is made to the extensive literature on the subject, see in particular Fiedler's "Lexikon der Hilfstoffe" (lexicon of adjuvants), 5th Edition, ECV Aulendorf 2002, which is incorporated herein by reference. These include, but are not limited to, fillers, binders, disintegrants, lubricants, glidants, stabilising agents, fillers or diluents, surfactants, film-formers, softeners, pigments and the like.

In a preferred embodiment the solid oral dosage form according to the present invention comprises as an additive a filler.

In a preferred embodiment the solid oral dosage form according to the present invention comprises as an additive, in addition to a filler, a disintegrant.

In a preferred embodiment the solid oral dosage form according to the present invention comprises as an additive, in addition to a filler and a disintegrant, a lubricant.

In a preferred embodiment the solid oral dosage form according to the present invention comprises as an additive, in addition to a filler, a disintegrant and a lubricant, a glidant. In a preferred embodiment the solid oral dosage form according to the present invention comprises as an additive, in addition to a filler, a disintegrant, a lubricant and a glidant, a binder.

As fillers one can in particular mention starches, e.g., potato starch, wheat starch, corn starch, hydroxypropyl cellulose, hydroxyethyl cellulose, hydroxypropyl methyl cellulose (HPMC) and, preferably, microcrystalline cellulose, e.g., products available under the registered trade marks AVICEL, FILTRAK, HEWETEN or PHARMACEL.

As binders for wet granulation, one can in particular mention polyvinylpyrrolidones (PVP), e.g., PVP K 30, HPMC, e.g., viscosity grades 3 or 6 cps, and polyethylene glycols (PEG), e.g., PEG 4000. A most preferred binder is PVP K 30.

As disintegrants one can in particular mention carboxymethylcellulose calcium (CMC-Ca), carboxymethylcellulose sodium (CMC-Na), crosslinked PVP (e.g. CROSPOVIDONE, POLYPLASDONE or KOLLIDON XL), alginic acid, sodium alginate and guar gum, most preferably crosslinked PVP (CROSPOVIDONE), crosslinked CMC (Ac-Di-Sol), carboxymethylstarch-Na (PIRIMOJEL and EXPLOTAB). A most preferred disintegrant is CROSPOVIDONE.

As glidants one can mention in particular colloidal silica, such as colloidal silicon dioxide, e.g., AEROSIL, magnesium (Mg) trisilicate, powdered cellulose, starch, talc and tribasic calcium phosphate or combinations of these with fillers or binders, e.g., silicified microcrystalline cellulose (PROSOLV). A very preferred glidant is colloidal silicon dioxide (e.g. AEROSIL 200).

As fillers or diluents one can mention confectioner's sugar, compressible sugar, dextrates, dextrin, dextrose, lactose, mannitol, microcrystalline cellulose, in particular, having a density of about $0.45 g/cm^3$, e.g., AVICEL, powdered cellulose, sorbitol, sucrose and talc. A most preferred filler is microcrystalline cellulose.

As lubricants one can mention in particular Mg stearate, aluminum (Al) or Ca stearate, PEG 4000 to 8000 and talc, hydrogenated castor oil, stearic acid and salts thereof, glycerol esters, Na-stearylfumarate, hydrogenated cotton seed oil and others. A most preferred lubricant is Mg stearate.

Additives to be used as filmcoating materials comprise polymers such as HPMC, PEG, PVP, polyvinylpyrrolidone-vinyl acetate copolymer (PVP-VA), polyvinyl alcohol (PVA), and sugar as film formers. A most preferred coating material is HPMC, especially HPMC 3 cps (preferred amount 5-6 mg/cm$^2$), and mixtures thereof with further additives, e.g., those available under the registered trade mark OPADRY. Further additives comprise pigments, dies, lakes, most preferred $TiO_2$ and iron oxides, anti-tacking agents like talcum and softeners like PEG 3350, 4000, 6000, 8000 or others. Most preferred additives are talcum and PEG 4000.

The present invention likewise relates to a solid oral dosage form comprising a therapeutically effective amount of a crystal form according to the invention and/or, preferably and, a form obtainable (especially obtained) therefrom during the manufacturing process of a correspondding pharmaceutical preparation, as an active ingredient, and a filler as an additive (pharmaceutically acceptable carrier material). Further additives include, but are not limited to, binders, disintegrants, lubricants, glidants, stabilising agents, diluents, surfactants, film formers, pigments, softeners and antitacking agents and the like. The amounts of the active ingredient and further additives are preferably those as defined above.

The present invention likewise relates to a solid oral dosage form comprising a therapeutically effective amount of a crystal form according to the invention, and/or, preferably and, a form obtainable (especially obtained) therefrom during the manufacturing process of a corresponding pharmaceutical preparation, as an active ingredient, and a filler and a disintergrant as additives. Further additives include, but are not limited to, binders, lubricants, glidants, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a therapeutically effective amount of a crystal form according to the invention, and/or, preferably and, a form obtainable (especially obtained) therefrom during the manufacturing process of a corresponding pharmaceutical preparation, as an active ingredient, and a filler, a disintegrant and a lubricant as additives. Further additives include, but are not limited to, binders, glidants, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a therapeutically effective amount of a crystal form according to the invention, and/or, preferably and, a form obtainable (especially obtained) therefrom during the manufacturing process of a corresponding pharmaceutical preparation, as an active ingredient, and a filler, a disintegrant, a lubricant and a glidant as additives. Further additives include, but are not limited to, binders, stabilising agents, diluents, surfactants, film formers, pigments, softeners and antitacking agents and the like. The amounts of the active ingredient and further additives are preferably those as defined herein above.

The present invention likewise relates to a solid oral dosage form comprising a crystal form according to the invention, and/or, preferably and, a form obtainable (especially obtained) therefrom during the manufacturing process of a corresponding pharmaceutical preparation, as an active ingredient, and a filler, a disintegrant, a lubricant, a glidant and a binder as additives. Further additives include, but are not limited to, stabilising agents, diluents, surfacetants, film formers, pigments, softeners and antitacking agents and the like. The amounts of the active ingredient and further additives are preferably those as defined herein above.

One or more of these additives can be selected and used by a person skilled in the art having regard to the particular desired properties of the solid oral dosage form by routine experimentation and without any undue burden.

The amount of each type of additive employed, e.g., glidant, binder, disintegrant, filler or diluent and lubricant or film coat may vary within ranges conventional in the art. Thus, for example, the amount of lubricant may vary within a range of from 0.2 to 5% by weight, in particular, for Mg stearate from 0.5 to 2.0% by weight, e.g., from 0.8 to 1.5% by weight; the amount of binder may vary within a range of from 0 to about 20% by weight, e.g., from 3 to 4% by weight; the amount of disintegrant may vary within a range of from 0 to about 20% by weight, e.g., from 13.5 to 16% by weight; the amount of filler or diluent may vary within a range of from 0 to about 80% by weight, e.g., from 20 to 32% by weight; whereas the amount of glidant may vary within a range of from 0 to about 5% by weight, e.g. from 0.4 to 0.6% by weight; and the amount of film coat may vary within a range of 0 to 20 mg/cm$^2$, e.g. 4 to 7 mg/cm$^2$.

It is a characteristic of the preferred solid oral dosage forms that they contain only a relatively small amount of additives given the high content of the active agent. This enables the production of physically small unit dosage forms. The total amount of additives in a given uncoated unit dosage may be about 60% or less by weight based on the total weight of the solid oral dosage form, more particularly about 54% or less. Preferably, the additive content is in the range of about 35 to 55% by weight, more particularly, the additive content ranges from about 50 to about 52% by weight.

A preferred amount of a filler, especially of microcrystalline cellulose, ranges from about 20 to 32% by weight per unit dosage form.

A preferred amount of a binder, especially of PVP K 30, ranges from about 3 to 4% by weight per unit dosage form.

A preferred amount of a disintegrant, especially of CROSPOVIDONE, ranges from about 13.5 to 15% by weight per unit dosage form.

A preferred amount of a glidant, especially of colloidal silicon dioxide, ranges from about 0.4 to 0.6% by weight per unit dosage form.

A preferred amount of a lubricant, especially of Mg stearate, ranges from about 0.8 to 1.5% by weight per unit dosage form.

A preferred amount of a film coat, especially of HPMC 3 cps, ranges from about 4 to 7 mg/cm$^2$ per unit dosage form.

Preferred amounts of aliskiren and additives are further shown in the illustrative Examples.

The absolute amounts of each additive and the amounts relative to other additives is similarly dependent on the desired properties of the solid oral dosage form and may also be chosen by the skilled artisan by routine experimentation without undue burden. For example, the solid oral dosage form may be chosen to exhibit accelerated and/or delayed release of the active agent with or without quantitative control of the release of active agent.

Thus, where accelerated release is desired a disintegrant such as crosslinked PVP, e.g., those products available under the registered trade marks POLYPLASDONE XL or KOLLIDON CL, in particular, having a molecular weight in excess of 1,000,000, more particularly, having a particle size distribution of less than 400 microns or, preferably, less than 74 microns, or comprising reactive additives (effervescent mixtures) that effect rapid disintegration of the tablet in the presence of water, for example so-called effervescent tablets that contain an acid in solid form, typically citric acid, which acts in water on a base containing chemically combined carbon dioxide, for example sodium hydrogencarbonate or sodium carbonate, and releases carbon dioxide.

Whereas if delayed release is desired one may employ coating technology for multiparticulates (e.g. pellets, minitablets), wax matrix systems, polymer matrix tablets or polymer coatings or other technologies conventional in the art.

Quantitative control of the release of the active agent can be achieved by conventional techniques known in the art. Such dosage forms are known as oral osmotic systems (e.g. OROS), coated tablets, matrix tablets, press-coated tablets, multilayer tablets and the like.

In a solid oral dosage form wherein the active agent consists of a crystal form according to the invention, and/or, preferably and, a form obtainable (especially obtained) therefrom during the manufacturing process of a corresponding pharmaceutical preparation, or a combination of aliskiren with other active pharmaceutical ingredients, preferred additives are microcrystalline cellulose, hydroxypropylcellulose, crosslinked PVP, PVP, PEG, CMC-Na or CMC-Ca, Mg stearate, Ca stearate or Al stearate, anhydrous colloidal silica, talc, titanium dioxide and iron oxide pigments. The amounts of additive employed will depend upon how much active agent is to be used. The stearate, e.g., Mg stearate is preferably employed in amounts of 0.8 to 1.5% by weight. Whereas the silica is preferably employed in an amount of from 0.4 to 0.6% by weight.

The amount of aliskiren in the form of the hemi-fumarate thereof within the total weight of the uncoated unit dosage form ranges, preferably, from about 83 to about 663 mg, most preferably, the amount of aliskiren hemi-fumarate is about 83, about 166 or about 332 mg per unit dosage form.

The amount of the binder within the total weight of the uncoated unit dosage form is preferably from 2 to 5%, most preferably from 3 to 4% by weight per unit dosage form.

The amount of the disintegrant within total weight of the uncoated unit dosage form is preferably from 0 to 20%, most preferably from 13.5 to 16% by weight per unit dosage form.

The amount of the glidant within the total weight of the uncoated unit dosage form is preferably from 0 to 5%, most preferably from 0.4 to 0.6% by weight per unit dosage form.

The amount of the lubricant within the total weight of the uncoated unit dosage form is preferably from 0.2 to 5%, most preferably from 0.8 to 1.5% for Mg stearate by weight per unit dosage form.

A preferred amount of a film coat, especially of HPMC 3 cps, is from about 4 to about 7 mg/cm$^2$ per unit dosage form.

The weight ratio of aliskiren to the binder preferably ranges from about 8:1 to about 25:1, more preferably from about 11:1 to about 15:1. Most preferably, the weight ratio is about 12.5:1.

The weight ratio of aliskiren to the disintegrant preferably ranges from about 2:1 to about 4:1, more preferably from about 2.5:1 to about 3.7:1. Most preferably, the weight ratio is about 3.1:1.

The weight ratio of aliskiren to the glidant preferably ranges from about 75:1 to about 125:1, more preferably from about 80:1 to about 90:1. Most preferably, the weight ratio is about 83.3:1.

The weight ratio of aliskiren to the lubricant preferably ranges from about 25:1 to about 63:1, more preferably from about 30:1 to about 50:1. Most preferably, the weight ratio is about 30:1.

The solid oral dosage forms according to the present invention may also be in the form of film-coated tablets or dragées in which case the solid oral dosage form is provided with a coating typically a polymer like HPMC, PVP or the like, sugar, shellac or other film-coating entirely conventional in the art. Attention is drawn to the numerous known methods of coating employed in the art, e.g., spray coating in a fluidized bed, e.g., by the known methods using apparatus available from Aeromatic, Glatt, Wurster or Hüttlin, in a perforated pan coater, e.g., by the known methods using apparatus from Accela Cota, Glatt, Driam or others, or other methods conventional in the art. The additives commonly used in confectioning may be employed in such methods.

A further embodiment of the present invention is a process for the manufacture of a pharmaceutical preparation (especially in a solid oral dosage form) according to the present inventtion, wherein a crystal form according to the invention (especially based on Modification A) is admixed with one ore more pharmaceutically acceptable carrier materials. The methods may comprise any of the manufacturing methods known in the art for pharmaceutical preparations, e.g. including wet granulation, slugging, spray drying spheronization or crystallization, coating or other steps.

Wet granulation of crystal forms according to the invention with excipients using water and/or an aqueous binder solution may lead to a change in polymorphism of the drug substance which changes e.g. partly to the amorphous state (indicated by "and/or, preferably and, a form obtainable (especially obtained) therefrom during the manufacturing process of a corresponding pharmaceutical preparation"), and may cause an inferior chemical stability of the drug product (DP). Nevertheless, also in these cases the use of a crystal form according to the invention as starting material for the manufacture of the corresponding pharmaceutical formulation is useful, as inter alia, the starting material then has more purity due to the crystallization, can be stored longer, can be dried better, can be filtered better after precipitation, has a better morphology for dosing and handling, and so on.

Anyway, wet granulation of a crystal form according to the invention using a mixture of organic solvents or an organic binder solution has been found to be a very advantageous way of manufacturing suitable aliskiren hemifumarate solid oral dosage forms, especially tablets, showing e.g. the following advantages:

Said wet granulation reduces the bulk volume of a aliskiren hemifumarate during granulation;

The influences of a changing drug substance quality are minimized;

A high drug loading above 46% by weight per unit dosage form may easily be achieved;

The formulation of tablets with sufficient hardness, resistance to friability, disintegration time, dissolution rate etc. is possible;

The sticking tendency and poor flow of the drug substance are reduced to a minimum;

A robust manufacturing process of the DP is achieved;

Scale-up of formulation and process resulting in a reproducible DP performance is achieved; and Sufficient stability to achieve a reasonable shelf life is achieved.

The excipients may be distributed partly in the inner (granular) phase and partly in the outer phase, which is the case in the described invention. Microcrystalline cellulose (filler) and CROSPOVIDONE (disintegrant) are partly in the inner and partly in the outer phase, PVP K 30 (binder) is only part of the inner phase, being the binder during granulation, whereas colloidal silicon dioxide (glidant) and Mg stearate (lubricant) are only part of the outer phase.

The inner phase excipients, e.g., filler, binder and disintegrant, and the drug substance are mixed and granulated with an ethanolic solution of the binder and additional ethanol. The granulate is dried and sieved. The outer phase containing, e.g., disintegrant, filler, glidant and lubricant, is screened with the dried granulate and mixed. The mixture is compressed into tablets. The cores may optionally be coated with a film-coat.

The granulate phase is defined as the inner phase, the excipients added to the granulate are defined as the outer phase of the tabletting mixture.

The invention likewise relates to a process for the preparation of solid oral dosage forms as described herein above. Such solid oral dosage form may be produced by working up components as defined herein above in the appropriate amounts, to form unit dosage forms.

Accordingly, the present invention provides a process for the manufacture of a solid oral dosage form of the present invention comprising:
1) mixing a crystal form according to the invention and additives and granulating said components with a granulation liquid;
2) drying a resulting granulate;
3) mixing the dried granulate with outer phase excipients;
4) compressing a resulting mixture to form a solid oral dosage as a core tablet; and
5) optionally coating a resulting core tablet to give a film-coated tablet.

Preferably, the additives in step (1) are selected from a filler, a disintegrant and a binder; and the outer phase excipients in step (3) are selected from a filler, a disintegrant, a lubricant and a glidant.

The granulation liquid can be ethanol, a mixture of ethanol and water, a mixture of ethanol, water and isopropanol, or a solution of PVP in the before mentioned mixtures. A preferred mixture of ethanol and water ranges from about 50/50 to about 99/1 (% w/w), most preferably it is about 94/6 (% w/w). A preferred mixture of ethanol, water and isopropanol ranges from about 45/45/5 to about 98/1/1 (% w/w/w), most preferably from about 88.5/5.5/6.0 to about 91.5/4.5/4.0 (% w/w/w). A preferred concentration of PVP in the above named mixtures ranges from about 5 to about 30% by weight, preferably from about 15 to about 25%, more preferably from about 16 to about 22%.

Attention is drawn to the numerous known methods of granulating, drying and mixing employed in the art, e.g., spray granulation in a fluidized bed, wet granulation in a high-shear mixer, melt granulation, drying in a fluidized-bed dryer, mixing in a free-fall or tumble blender, compressing into tablets on a single-punch or rotary tablet press.

The manufacturing of the granulate can be performed on standard equipment suitable for organic granulation processes. The manufacturing of the final blend and the compression of tablets can also be performed on standard equipment.

For example, step (1) may be carried out by a high-shear granulator, e.g., Collette Gral; step (2) may be conducted in a fluid-bed dryer; step (3) may be carried out by a free-fall mixer (e.g. container blender, tumble blender); and step (4) may be carried out using a dry compression method, e.g., a rotary tablet press.

As described above, the core tablets may then be optionally film-coated.

Due to the high hygroscopicity and water sensitivity of crystal forms of the invention with respect to changes in polymorphism, the use of water has preferably to be avoided in order to prevent the drug substance from changes in polymorphism for the above stated reasons (amorphous state, inferior chemical stability). A solution for said problem is to apply an organic film-coating process.

It was found that an aqueous film coating process using a standard film-coat composition can be applied to aliskiren core tablets without further changes in polymorphism.

The film-coat preferably consists of HPMC as the polymer, iron oxide pigments, titanium dioxide as coloring agent, PEG as softener and talc as anti-tacking agent. The use of coloring agents or dyes may serve to enhance the appearance as well as to identify the compositions. Other dyes suitable for use typically include carotinoids, chlorophyll and lakes.

The film coating conditions have to assure that the tablet cores do not take up considerable amounts of moisture and that the drug substance within the tablets does not closely get into contact with water droplets. This is achieved by process parameter settings that reduce the amount of humidity which gets onto the tablet cores.

The solid oral dosage forms of the present invention are useful for lowering the blood pressure, either systolic or diastolic or both, and/or in addition for the treatment of any one or more of the other diseases/disorders mentioned herein.

The present invention likewise relates to a method of treating hypertension (whether of the malignant, essential, renovascular, diabetic, isolated systolic, or other secondary type), and/or any one or more of the other diseases/disorders mentioned herein.

In the present application the terms "(pharmaceutical) composition" and "(pharmaceutical) formulation" have the same meaning.

The invention relates especially to the embodiments given in the claims, especially in the dependent claims. The claims are therefore incorporated herein by reference.

The invention in particular relates to the crystal forms and pharmaceutical formulations given in the Examples, especially to Modification A and pharmaceutical formulations comprising it as given in the Examples.

The invention is illustrated in particular by the examples and also relates to the new crystal forms named in the examples and to their usage and to methods for the preparation thereof.

The following examples serve to illustrate the invention without limiting the invention in any way. "SPP 100" is aliskiren, the hemifumarate thereof is also occasionally referred to as drug substance (DS). Ethanol ALI is technical grade ethanol.

DSC=Differential Scanning Calorimetry
TG=TGA=Thermogravimetry (Analysis)
XRPD=X-Ray Powder Diffraction

TABLE 1

Table of methods and conditions used (if not mentioned otherwise)

| | |
|---|---|
| TG-method | |
| Instrument | TGA851e Mettler Toledo STAR System |
| Nitrogen flow | 50 ml/min |
| DSC-method | |
| Instrument | Perkin Elmer, Pyris |
| Nitrogen flow | 20 ml/min |
| XRPD-method | |
| Instrument | X1 or XDS2000; Scintag INC |
| Irradiation | CuKα (45 kV, 40 mA) |
| Divergence slice | 3 mm and 2 mm |
| Measuring slice | 0.3 mm and 0.2 mm |
| Chopper | 0.02 degree |
| Scan mode | Reflection |
| Scan type | Continuous scan |
| Scan rate | 0.5/min (2Theta value) |
| Scan range | 2°-40° (2Theta value) |
| Instrument | STOE Powder Diffraction System |
| Irradiation | CuKα (50 kV, 30 mA) |
| Detector | Linear PSD |
| Scan mode | Transmission |
| Scan type | Step scan |
| Scan range | 2°-40° (2Theta value) |
| IR-method | |
| Instrument | FT-IR Bruker IFS-55 |
| Detector | TGS |
| Mode | Transmission |
| Scan range | 4000 $cm^{-1}$-400 $cm^{-1}$ |
| Technique | Nujol between two KBr plates and KBr disc |
| RAMAN | |
| Instrument | Bruker IFS-100S |

TABLE 1-continued

Table of methods and conditions used (if not mentioned otherwise)

Microcalorimetry

| Instrument | Thermal Activity Monitor, Thermometrics, Järvälla, Sweden |
|---|---|
| Microscopy | |
| Instrument | Jeol JSM 6300 |

EXAMPLE 1

Crystal Modification A (also called Form A)

40 g of SPP100 base is dissolved in 51 g of ethanol ALI. A solution of fumaric acid in ethanol ALI (2 g/46 g) at 35° C., is dropped at room temperature to the base in 20 min. The solution is heated and a part of ethanol is distilled until the ratio SPP/EtOH 1/0.9 is reached. Then 30 g of acetonitrile is added at 50° C. with 1.7 g of ethanol to adjust the ratio EtOH/CH$_3$CN to 40/60. Additional 98 g of acetonitrile is added at T>37° C. to reach the ratio CH$_3$CN/EtOH 87/13. The solution is seeded at 37° C. with 0.5 ml of SPP100 modification A in suspension (obtained e.g. from equilibration experiments as in Example 10 f) (iv) and is cooled down from 37° C. to 17° C. in 200 min. The suspension is stirred 20 min and then heated up from 17° C. to 37° C. in 40 min. and stirred for 10 min. The suspension is cooled down from 37° C. to 17° C. for 200 min., stirred for 20 min and heated up from 17 to 37° C. in 40 min. After 10 minutes under stirring the suspension is cooled down to 22° C. in 200 min and stirred for 20 min. The suspension is distilled off and 115 g of CH$_3$CN is added at 20° C. The suspension is cooled down at 3° C. in 180 min and filtrated. The solid is washed with a portion of the mother liquor to obtain Crystal Modification A of aliskiren hemifumarate.

Characterisation:

The form is a dried product of solvated form S$_A$ obtained in acetonitrile/ethanol mixtures (Example 2).

a) Differential Scanning Calorimetry (DSC) Studies: Influence of Heating Rate

TABLE 2

Modification A Instrument: Mettler Toledo DSC822e (Nr. 17-1), heating rate: 10 K/min

| | Melting (° C.) | Enthalpy (J/g) |
|---|---|---|
| Mean value: X = 6 | 96.6 | 29 |

According to the heating rate applied, the presence of an additional thermal event can be observed at about 60° C. corresponding to the glass transition. The presence of amorphous part in modification A is also observed by X Ray powder diffraction (XRPD) (calculated to be approximately 50%).

b) X Ray Powder Diffraction (XRPD)

A batch of Modification A shows an X-Ray pattern with the following peaks (under the conditions given in the description to FIG. 1): Peaks (°2Theta): 6.0, 7.3, 8.6, 9.2, 9.9, 15.0, 17.2 and 17.9, e.g. in more detail 6.0, 7.3, 8.6, 9.2, 9.9, 15.0, 17.2, 17.9, 19.2, 19.7, 20.1. For example, a batch shows the X-Ray diffraction pattern given in FIG. 1.

c) X-ray Powder Diffraction Study of Modification A at Various Relative Humidities (RH)

The aim is to evaluate the influence of the storage condition on the crystalline form of SPP100 hemifumarate For this purpose, two different experiments have been performed. The first one consists to submit SPP100 hemifumarate modification A to a nitrogen flow and to record at various time the corresponding XRPD pattern. During the second experiment the influence of relative humidity on the crystalline modification A is determined by XRPD measurement. The corresponding results have been summarized in the following tables.

TABLE 3

Storage under nitrogen flow

| | Time (hour) | | | | | |
|---|---|---|---|---|---|---|
| | 0.00 | 2.25 | 4.53 | 7.80 | 13.10 | 14.75 |
| XRPD Change | Mod A none | Mod A none | Mod A none | Mod A none | Mod A none | Mod A none |

Comment: No change of the modification is observed during storage under nitrogen flow.

TABLE 4

Influence of relative humidity Modification A

| | Time (h) | | | | | | | | |
|---|---|---|---|---|---|---|---|---|---|
| | 0 | 2.55 | 5.01 | 7.4 | 9.8 | 24.23 | 26.86 | 32.51 | 47.6 | 143.9 |
| RH (%) | 0%* | 10% | 25% | 35% | 45% | 45% | 60% | 70% | 70% | 70% |
| XRPD | Mod A | Mod A | Mod A | Mod A | Mod A | Mod A | Mod A | Mod A | Mod A | Mod A |

Comment: No significant variation is observed.

EXAMPLE 2

Solvate S$_A$ (also called Crystal Form E)

The solvated form of modification A before drying is obtained as described in Example 1 but the suspension (CH$_3$CN/EtOH 87/13 w/w) is not filtrated.

X Ray Powder Diffraction (XRPD)

A batch of Solvate S$_A$ shows an X-Ray diffraction pattern with the following peaks (under the conditions given in the description to FIG. 4): Peaks (°2Theta): 4.5, 5.9, 7.1, 14.8, 16.8, 18.0, 19.1 and 20.7, e.g. in more detail 4.5, 5.9, 7.1, 8.6, 9.1, 11.0, 11.2, 13.2, 14.2, 14.8, 15.2, 16.0, 16.4, 16.8, 18.0, 19.1, 19.7, 20.7, 21.4, 22.4, 22.6, e.g. a batch shows the XRPD given in FIG. 4.

EXAMPLE 3

Crystal Modification B (also called Form B)

This crystal form is obtained from 150 g of SPP100 hemifumarate dissolved in 281 g of Ethanol ALI at 55° C. To this solution, 1125 g of $CH_3CN$ is dropped, and the solution is left at 30 minutes at 37° C. The solution is cooled down at 35° C., after 1 hour, the solution becomes slightly cloudy. The solution (ratio $CH_3CN$/ethanol=80/20 w/w) is cooled down to 20° C. in 200 min, and the suspension is left at room temperature. After crystallization of the substance, the suspension is filtrated and the solid dried for 2 days under 10 mbar at 40° C., and Crystal Modification B of aliskiren hemifumarate is obtained.

Characterisation:

The form Modification B is a dried product of solvated form $S_B$ obtained in acetonitrile/ethanol mixtures (Example 2).

a) DSC Studies:

TABLE 5

Modification B Instrument: Mettler Toledo DSC822e (Nr. 17-1), heating rate: 10 K/min

|  |  | Melting (° C.) | Enthalpy (J/g) |
|---|---|---|---|
| Mean value: | X = 6 | 100.7 | 56 |

DSC experiments do not show presence of amorphous part in modification B.

b) X Ray Powder Diffraction (XRPD)

A batch of Modification B shows an X-Ray diffraction pattern with the following peaks (under the conditions given in the description to FIG. 2): Peaks (°2Theta): 3.8, 6.5, 7.7, 8.0, 15.6 and 17.4, e.g. in more detail 3.8, 6.5, 7.7, 8.0, 13.8, 14.5, 15.6, 17.4; e.g. a batch shows the XRPD given in FIG. 2.

EXAMPLE 4

Solvate Form $S_B$

The solvated form of modification B before drying is obtained as described in Example 3 but the suspension ($CH_3CN$/EtOH 80/20 W//W) is not filtrated.

X Ray Powder Diffraction (XRPD)

A batch of Solvate $S_B$ shows an X-Ray diffraction (under the conditions given in the description for FIG. 5) with the following Peaks: Peaks (°2Theta): 6.7, 7.2, 8.0, 12.2, 15.6, 16.9, 17.3 and 18.3, e.g. in more detail 3.7, 6.1, 6.4, 6.7, 7.2, 8.0, 10.0, 11.1, 12.2, 15.6, 16.9, 17.3, 18.3, 18.7, 19.5; thus, a batch shows an XRPD represented in FIG. 5.

EXAMPLE 5

Solvate Forms $S_C$ and $S_D$, Single Crystals

Characterisation: Structurally, solvate forms $S_C$ and $S_D$ are characterized by single crystal X-ray diffraction. The single crystals are grown using heptane as antisolvent. The isopropanol and the ethanol solvate of SPP100 hemifumarate can be grown as small needles from isopropanol, or ethanol solution respectively, by precipitation with heptane antisolvent. As there the data quality is better, only the ethanol solvate form obtained from ethanol/heptane (so called $S_D$, corresponding to Form D mentioned in Example 9) is discussed in detail. But from the data the conclusion can be drawn that the isopropanol solvate (so called $S_C$) is isostructural to the ethanol solvate (when heptane is used as antisolvent). The solvate $S_D$ stoichiometry consists of one SPP100 molecule, 1/2 fumarate group and 3 solvent molecules.

The structures of $S_C$ and $S_D$ are both very sensible to air and humidity and decompose rapidly. They consist of a distinct channel structure along the crystallographic b-axis which occupies about 25% of the whole crystal structure volume. Within the channels the solvent molecules can be found which exhibit strong disorder. Hydrogen bonds can be found between SPP100 (hydroxyl group and protonated amine group of SPP100) and the fumarate group and between SPP100 molecules (protonated amine group and oxygen). Another H-bond exists between ethanol and SPP100 (oxygen and amine group). Dominating propagation vector of the H-bonds is the crystallographic b-axis. Although some H-bonds can be found the main packing force (for a 3-dim crystal) of the structure seems to be Van der Waals interactions which accounts for the instability of the structure.

TABLE 6

Crystal data of SPP100 hemifumarate solvate form with ethanol $S_D$

| | Ethanol (antisolvent heptane) |
|---|---|
| Crystal system | Orthorhombic |
| Space group | $P\ 2_1 2_1 2$ |
| a, Å | 20.114(9) |
| b, Å | 12.497(5) |
| c, Å | 17.596(8) |
| V, Å$^3$ | 4423(3) |
| $D_{calc}$, g cm$^{-3}$ | 1.169 |
| Z | 4 |
| radiation, Å | 1.5406 |
| Θ range, ° | 2.51-54.23 |
| no. variables refined | 495 |
| no. restraints | 75 |
| no. reflect. refined | 5359 |
| GOF | 1.052 |
| Final $R_1$ [I > 2σ(I)] | 0.0783 |
| Final $wR_1$ [I > 2σ(I)] | 0.1992 |

GOF = Goodness of Fit.

EXAMPLE 6

Amorphous Material

Amorphous SPP 100 hemifumarate is obtained by spray drying a solution of 100 g of SPP100 in 400 g of ethanol ALI. About 80 g of amorphous SPP100 hemifumarate is obtained after spray drying. The solid is dried under 20 mbar at 30° C. and stored under nitrogen atmosphere.

Characterisation:

a) DSC Studies

Instrument: Perkin Elmer pan: 219-041, temperature range: 10° C. to 140° C. The glass transition of amorphous SPP100 hemifumarate is observed at about 60° C. The ΔH melting change can be found as approx. $\Delta c_p$=0.5 J/g ° C.

b) X Ray Powder Diffraction (XRPD)

A batch of amorphous aliskiren hemifumarate shows the X-Ray diffraction pattern given in FIG. 3. No significant peaks can be observed.

EXAMPLE 7

Further Physico-Chemical Characterisation of Crystal Modifications A, Crystal Modification B and Amorphous Material Results obtained with Crystal Modifications (=Forms) A and B/dry) are characterized in a summarized form in the following tables and descriptions:

A) General Analytical Data

Proton and $^{13}C$ NMR data as well as IR and Elemental Analysis data confirm the structure of aliskiren hemifumarate (details not shown).

B) Dynamic Vapor Sorption Isotherm of Modification A, Modification B and Amorphous Material:

In the following tables 7 and 8, R.H. stands for Relative Humidity, Sorpt. for Sorption and Desorpt. for Desorption.

TABLE 7

|  | Modification A | |
| --- | --- | --- |
| R.H. (%) | Sorpt. wt % $1^{st}$ | Desorpt wt % $2^{nd}$ |
| 0 | 0.00 | −0.03 |
| 10 | 0.84 | 1.37 |
| 20 | 1.50 | 2.06 |
| 30 | 2.09 | 2.60 |
| 40 | 2.72 | 3.16 |
| 50 | 2.54 | 3.85 |
| 60 | 4.72 | 4.72 |
| 70 | / | / |
| 80 | / | / |
| 92 | / | / |

TABLE 8

|  | Modification A | | Modification B | |
| --- | --- | --- | --- | --- |
| R.H. (%) | Sorpt. wt % $1^{st}$ | Desorpt wt % $2^{nd}$ | Sorpt. wt % $1^{st}$ | Desorpt wt % $2^{nd}$ |
| 0 | 0.00 | −0.52 | 0.00 | 0.04 |
| 10 | 0.53 | 0.43 | 0.94 | 2.33 |
| 20 | 0.76 | 0.77 | 1.69 | 3.17 |
| 30 | 1.01 | 1.09 | 2.53 | 3.76 |
| 40 | 1.30 | 1.44 | 3.68 | 4.47 |
| 50 | 1.77 | 1.97 | 5.52 | 5.65 |
| 60 | 2.66 | 2.66 | 7.68 | 7.68 |
| 70 | / | / | / | / |
| 80 | / | / | / | / |
| 92 | / | / | / | / |

Comment: SPP100 hemifumarate Modification A, Modification B and amorphous form show a strong hygroscopic behavior. The water uptake is reversible for maximum relative humidity of 60%. Above this value, SPP100 hemifumarate Modification A, Modification B and amorphous form show a significant increase of the relative humidity until the substance becomes a solution.

The continuous increase/decrease of the water sorption/desorption suggests a cooperative hydration/dehydration without destruction of the crystal structure. This behavior could be due to the presence either of channels or of layers in the crystal structure. The ability of the material to accept water molecules can have a significant effect on its crystallinity as the crystal structure is always submitted to physical stress.

Up to a certain relative humidity (60% R.H. at 25° C.) the hygroscopicity of SPP100 hemifumarate modification A, modification B and amorphous is reversible. Above 60% R.H., the compound becomes deliquescent. This phenomenon is connected with the high solubility of the material in the water.

Modification B is out of these 3 modifications the least hygroscopic form. The lower affinity with water can be explained by a different crystal structure. For a relative humidity higher than 60% R.H. at 25° C., the same behavior as modification A and amorphous is observed which is due to a dissolution of the material in water.

C) Heat of Dissolution

About 100 mg of material is placed in a sealed glass ampoule. After equilibration at 25° C., the ampoule is broken in 100 ml of water. The heat produced during the dissolution is measured and the mean of three determinations is given in Table 9:

TABLE 9

|  | Modification A (KJ/mol) | Modification B (KJ/mol) | Amorphous (KJ/mol) | Amorphous (KJ/mol) |
| --- | --- | --- | --- | --- |
| Mean | −31.6 | −24.6 | −35.1 | −38.1 |

Comment:
There is no significant variation between amorphous and modification A.

D) Comparison of Analytical Methods and Limits of Detection:

(i) Modification B in Modification A

XRPD: SPP100 hemifumarate identity by XRPD: Modification B can be detected in mixtures with SPP100 hemifumarate Modification A with a Limit of Detection (LOD) of better than 4%.

FT-IR:

Modification B can be distinguished from modification A in FT-IR technique using the bands in the area 1465 $cm^{-1}$. However, there is a strong similarity between FT-IR spectra of modification A and modification B.

FT-RAMAN:

Modification B can be distinguished from modification A by FT-Raman. However, modification B does not present a typical band in comparison to the FT-RAMAN spectrum of modification A.

(ii) Amorphous Part in Modification A

XRPD: SPP100 hemifumarete amorphous content by XRPD: Quantification of amorphous content SPP100 hemifumarate is possible by X-ray powder diffraction (XRPD). FT-IR and FT-RAMAN spectroscopy: FT-IR and the FT-RAMAN spectra do not present significant difference between amorphous SPP100 hemifumarate material and SPP100 hemifumarate modification A, to develop a quantitative method.

Dynamic Vapor Sorption (DVS): A linear relationship between the amorphous content present in the sample and the water uptake can be observed from several mixture performed using modification A and amorphous material.

EXAMPLE 8

Crystal Form C

This crystal form is obtained by equilibration from solvents mixture of ethanol/acetone, and corresponds to a mixture between Modification A and a degradation product obtained by chemical reaction with acetone (Schiff Base Formation). It is therefore is not considered further here. With other ketones (e.g. methyl ethyl ketone, 5-nonanone, cyclohexanone), also chemical reaction products (presumably also Schiff bases) are found.

EXAMPLE 9

Crystal Form D

Form D is obtained by crystallization in tetrahydrofurane (equilibration and drying), it corresponds to the group so called solvates Type III Example 11 a) (i).

EXAMPLE 10

Further Characterisation of Solvate Forms $S_A$ and $S_B$, Modifications A and B and Other Forms by Desolvation/Drying Study of Solvate Forms $S_A$ and $S_B$: Equilibrium Experiments Between 200 mg to 700 mg of drug substance are equilibrated with 0.5 to 1 ml of solvent for at least 24 h in a water bath at the determined temperature +/−0.1° C. After equilibration, the solutions are filtered. The solid part is investigated by XRPD (X-ray Powder Diffraction).

TABLE 10

Equilibrations at 25 degree Celsius of Modification A

| Solvents | XRPD |
| --- | --- |
| Acetone | + chemical reaction |
| Acetonitrile | − |
| Cyclohexane | − |
| Dichloromethane | // |
| Dioxane | + Typ III |
| DMF | // |
| DMAc | + Typ III |
| Ethanol | // |
| n-heptane | − |
| Isopropanol | + Mod. B |
| Methylethylketone | + chemical reaction |
| Pentanol | + Typ V |
| TBME | + amorphous + Typ II |
| Tetrahydrofurane | + Typ III |
| Toluol | + amorphous |

Meaning of symbols:
// not carried out as substance too soluble
+ change detected
− no change detected
Comment:
Equilibration in acetonitrile, cyclohexane and n-heptane does not show a conversion of modification A.

EXAMPLE 11

Other Solvate Forms of SPP 100 Hemifumarate a) Solvate Forms Similar to Modification A:
   (i) Type III (corresponds to Crystal Form D) This crystalline form is obtained from Modification A equilibrated at 25° C. in dioxane and in tetrahydrofurane. It can also be obtained from amorphous material kept under THF atmosphere at 25° C. The XRPD pattern presents a correct crystallinity with the presence of well resolved peaks at low theta. A batch of Type III shows an X-Ray diffraction pattern (under the conditions given in the description for FIG. 6) with the following Peaks (°2Theta): 5.4, 7.4, 8.7, 9.1, 10.3, 15.4, 16.0 and 18.2, e.g. in more detail 5.4, 7.4, 8.7, 9.1, 10.3, 11.3, 11.7, 12.3, 14.2, 15.1, 15.4, 16.0, 16.6, 17.8, 18.2, 19.4, 19.9, 20.2; e.g. an XRPD as given in FIG. 6.

(ii) Type IV: This solvate is obtained from amorphous material stored under acetonitrile atmosphere at room temperature. The beginning of the XRPD pattern of this crystalline form is similar to the one observed for Modification A. A batch of Type IV shows an X-Ray diffraction pattern (under the conditions given in the description for FIG. 7) with the following peaks: Peaks (°2Theta): 4.5, 5.9, 7.2, 8.6, 9.2, 10.0, 11.1, 15.0 and 16.0, e.g in more detail 4.5, 5.9, 7.2, 8.6, 9.2, 10.0, 11.1, 11.6, 15.0, 16.0, 17.4, 17.9, 19.2, 21.7; e.g. an XRPD as given in FIG. 7.

(iii) Type VI: This solvate is obtained from Modification A kept under ethanol (absolute or ALI) atmosphere, or under methanol atmosphere. This modification shows a good crystallinity with the presence of sharp peaks at low 2Theta. A batch of Type VI shows an X-Ray diffraction pattern (under the conditions given in the description for FIG. 8) with the following peaks: Peaks (°2Theta): Peaks (°2Theta): 4.6, 5.9, 7.1, 9.2, 11.2, 14.8, 16.4, 16.9 and 19.2, e.g. in more detail 4.6, 5.9, 7.1, 8.4, 9.2, 11.2, 11.6, 12.1, 12.8, 14.8, 16.4, 16.9, 18.5, 19.2, 19.8, 20.8, 21.4, 21.8, 23.3; e.g. an XRPD as given in FIG. 8.

b) Solvate Forms Similar to Modification B:
   (i) Type I: This solvate is obtained by crystallization from amorphous material under solvent vapor of ethyl acetate or methyl acetate at room temperature. The XRPD pattern presents a very low crystallinity and shows some similarity with Modification B. A batch of Type I shows an X-Ray diffraction pattern (under the conditions given in the description for FIG. 8) with the following peaks: Peaks (°2Theta): 6.5, 8.0, 14.6 and 15.5; e.g. an XRPD as given in FIG. 9.

(ii) Type II: This solvate is obtained from Modification A and amorphous material equilibrated at 25° C. in TBME (tert-butyl-methyl ether) atmosphere. The XRPD pattern presents a low crystallinity. The beginning of the spectrum presents some similarity with Modification B. A batch of Type II shows an X-Ray diffraction pattern (under the conditions given in the description for FIG. 10) with the following peaks: Peaks (°2Theta): 4.4, 6.7, 15.4 and 16.6, e.g. in more detail 4.4, 6.7, 9.4, 11.6, 15.4, 16.6, 19.7; e.g. an XRPD as given in FIG. 10.

(iii) Type V: This form is obtained from Modification A equilibrated in pentanol atmosphere at 25° C. and from amorphous material kept under room temperature under n-butanol, 2-propanol, 1-hexanol and ethanol atmosphere. This type is very close to Modification B (only some shift of the peak positions and sometimes presence of additional peak). Medium crystallinity. A batch of Type V shows an X-Ray diffraction pattern (under the conditions given in the description for FIG. 11) with the following peaks: Peaks (°2Theta): 3.7, 6.5, 8.0, 14.6, 15.5, 17.2, 18.8 and 20.1, e.g. in more detail 3.7, 6.3, 6.5, 7.2, 8.0, 9.6, 10.1, 12.4, 14.6, 15.1, 15.5, 17.2, 17.7, 18.8, 19.3, 19.6, 20.1, 22.1, 23.1; e.g. an XRPD as given in FIG. 11.

For example, about 100 mg of amorphous material are placed under organic solvent vapor for at least one week at room temperature. The solid material is investigated by XRPD (X-ray powder diffraction), and the following results are obtained:

TABLE 11

Results from keeping amorphous material under solvent vapor:

| Solvents | Modification obtained by XRPD |
| --- | --- |
| Acetonitrile | + Typ. IV |
| n-butanol | + Typ. V |
| Dimethylformamide | Mainly amorphous |
| Ethanol | Amorphous + Typ. V |
| Ethyl acetate | + amorphous + small amount of Typ. III |
| 1-hexanol | + Typ V |

TABLE 11-continued

Results from keeping amorphous material under solvent vapor:

| Solvents | Modification obtained by XRPD |
|---|---|
| Methyl acetate | + Typ I |
| 2-propanol | + Typ V |
| TBME | – |
| Tetrahydrofurane | + Typ III |
| Toluene | – |

EXAMPLE 12

Pharmaceutical Preparations

The following formulation examples of pharmaceutical preparations are prepared using an active ingredient starting material with crystal form A (Modification A) of aliskirene hemifumarate in a wet granulation preparation process:

Crystal Form A (though not yet obtained without amorphous material) is preferably used in the preparation of pharmaceutical preparations in a wet granulation process as decribed above in the general part of the disclosure.

Alternatively, though this crystal form is inclined to form bundles of needle-like crystals, Crystal Form B is also preferably used.

TABLE 12

Composition of aliskiren 150 mg (free base) uncoated tablets in mg/unit.

| Component | Roller compacted tablet | Dosage form 1 | Dosage form 2 | Dosage form 3 |
|---|---|---|---|---|
| Aliskiren hemi-fumarate | 165.750 | 165.750 | 165.750 | 165.750 |
| Microcrystalline cellulose | 220.650 | 84.750 | 72.250 | 107.250 |
| Polyvinylpyrrolidon K 30 | — | — | 12.000 | 12.000 |
| Crospovidone | 84.000 | 45.000 | 44.000 | 48.200 |
| Aerosil 200 | 4.800 | 1.500 | 1.500 | 1.800 |
| Magnesium stearate | 4.800 | 3.000 | 4.500 | 5.000 |
| Total weight | 480.000 | 300.000 | 300.000 | 340.000 |

TABLE 13

Composition of aliskiren 150 mg (free base) uncoated tablets in % by weight.

| Component | Roller compacted tablet | Dosage form 1 | Dosage form 2 | Dosage form 3 |
|---|---|---|---|---|
| Aliskiren hemi-fumarate | 34.53 | 55.25 | 55.25 | 48.75 |
| Microcrystalline cellulose | 45.97 | 28.25 | 24.08 | 31.545 |
| Polyvinylpyrrolidon K 30 | — | — | 4 | 3.53 |
| Crospovidone | 17.5 | 1.5 | 14.67 | 14.175 |
| Aerosil 200 | 1 | 0.5 | 0.5 | 0.53 |
| Magnesium stearate | 1 | 1 | 1.5 | 1.47 |
| Total % | 100.00 | 100.00 | 100.00 | 100.00 |

TABLE 14

Composition of aliskiren 150 mg (free base) uncoated tablets in mg/unit (divided into inner/outer phase).

| | Component | Roller compacted tablet | Dosage form 1 | Dosage form 2 | Dosage form 3 |
|---|---|---|---|---|---|
| Inner Phase | Aliskiren hemifumarate | 165.75 | 165.75 | 165.75 | 165.75 |
| | Microcrystalline cellulose | 220.65 | 84.75 | 72.25 | 90.25 |
| | Polyvinylpyrrolidon K 30 | — | — | 12.00 | 12.00 |
| | Crospovidone | 36.00 | — | — | 14.20 |
| | Aerosil 200 | — | — | — | — |
| | Magnesium stearate | 2.40 | — | — | — |
| Outer phase | Crospovidone | 48.00 | 45.00 | 44.00 | 34.00 |
| | Microcrystalline cellulose | — | — | — | 17.00 |
| | Aerosil 200 | 4.80 | 1.50 | 1.50 | 1.80 |
| | Magnesium stearate | 2.40 | 3.00 | 4.50 | 5.00 |
| | Total weight | 480.00 | 300.00 | 300.00 | 340.00 |

TABLE 15

Composition of aliskiren 150 mg (free base) uncoated tablets in % by weight (divided into inner/outer phase).

| | Component | Roller compacted tablet | Dosage form 1 | Dosage form 2 | Dosage form 3 |
|---|---|---|---|---|---|
| Inner Phase | Aliskiren hemifumarate | 34.53 | 55.25 | 55.25 | 48.75 |
| | Microcrystalline cellulose | 45.97 | 28.25 | 24.08 | 26.545 |
| | Polyvinylpyrrolidon K 30 | — | — | 4 | 3.530 |
| | Crospovidone | 7.5 | — | — | 4.175 |
| | Aerosil 200 | — | — | — | — |
| | Magnesium stearate | 0.5 | — | — | — |
| Outer phase | Crospovidone | 10 | 15 | 14.67 | 10 |
| | Microcrystalline cellulose | — | — | — | 5 |
| | Aerosil 200 | 1 | 0.5 | 0.5 | 0.53 |
| | Magnesium stearate | 0.5 | 1 | 1.5 | 1.47 |
| | Total % | 100.00 | 100.00 | 100.00 | 100.00 |

EXAMPLE 13

Composition (Obtained by Wet Granulation)

TABLE 16

Composition of aliskiren (in one of the modifications or forms mentioned above, especially Modification A) (dosage form 3), film-coated tablets in mg/unit.

| | Dosage form 3/Strength | | |
|---|---|---|---|
| Component | 75 mg (free base) | 150 mg (free base) | 300 mg (free base) |
| Aliskiren hemi-fumarate | 82.875 | 165.750 | 331.500 |
| Microcrystalline cellulose | 53.625 | 107.250 | 214.500 |
| Polyvinylpyrrolidon K 30 | 6.000 | 12.000 | 24.000 |
| Crospovidone | 24.100 | 48.200 | 96.400 |

TABLE 16-continued

Composition of aliskiren (in one of the modifications or forms mentioned above, especially Modification A) (dosage form 3), film-coated tablets in mg/unit.

| Component | Dosage form 3/Strength | | |
|---|---|---|---|
| | 75 mg (free base) | 150 mg (free base) | 300 mg (free base) |
| Aerosil 200 | 0.900 | 1.800 | 3.600 |
| Magnesium stearate | 2.500 | 5.000 | 10.000 |
| Total tablet weight | 170.000 | 340.000 | 680.000 |
| Opadry premix white | 9.946 | 16.711 | 23.9616 |
| Opadry premix red | 0.024 | 0.238 | 1.8382 |
| Opadry premix black | 0.030 | 0.051 | 0.2002 |
| Total film-coated tablet weight | 180.000 | 357.000 | 706.000 |

What is claimed is:

1. A crystal form of aliskiren hemifumarate characterized by an X-Ray powder diffraction pattern showing main peaks at degrees 2Theta +/−0.3 degrees: 3.8, 6.5, 7.7, 8.0, 15.6 and 17.4.

2. The crystal form of claim 1, additionally characterized by X-Ray powder diffraction peaks at degrees 2Theta +/−0.3 degrees: 13.8 and 14.5.

3. The crystal form of claim 1 or claim 2, wherein the crystal form is a solvate form.

4. The crystal form of claim 1, having a melting point in the range from about 95 to about 105° C.

5. The crystal form of claim 4, having a melting point in the range from about 99 to about 102° C.

6. The crystal form of claim 4, wherein the heating rate is about 10 K/min.

7. The crystal form of claim 1, having a purity of at least about 20% by weight.

8. The crystal form of claim 7, having a purity of at least about 30% by weight.

9. The crystal form of claim 8, having a purity of at least about 40% by weight.

10. The crystal form of claim 9, having a purity of at least about 50% by weight.

11. The crystal form of claim 1, having a purity of at least about 90% by weight, related to total aliskiren hemifumarate.

12. The crystal form of claim 11, having a purity of at least about 95% by weight, related to total aliskiren hemifumarate.

13. The crystal form of claim 1, which is obtainable from a solution with a w/w ratio of acetonitrile:ethanol from about 90:10 to about 75:25.

14. The crystal form of claim 13, which is obtainable from a solution with a w/w ratio of acetonitrile:ethanol of about 80:20.

15. The crystal form of claim 13, wherein the solution has a temperature from about 15° C. to about 40° C.

16. The crystal form of claim 15, wherein the solution has a temperature from about 35° C. to about 37° C.

17. The crystal form of claim 15, wherein the solution has a temperature of about 20° C., and the aliskiren hemifumarate crystallizes and is filtered and dried under vacuum.

18. The crystal form of claim 17, wherein the vacuum is under 10 mbar at 40° C.

19. The crystal form of claim 13, having a melting enthalpy of about 56±8 J/g at a heating rate of 10 K/min.

20. The crystal form of claim 13, having a melting enthalpy of about 56±8 J/g at a heating rate of 10 K/min and is obtainable from a solution with a w/w ratio of acetonitrile:ethanol of about 80:20, wherein the solution has a temperature of about 20° C., the aliskiren hemifumarate crystallizes and is filtered and dried under a vacuum under 10 mbar at 40° C.

21. A method of treating a disease in a warm-blooded animal that can be modulated by blocking the $AT_1$ receptor by administering the crystal form of claim 1.

22. A method of making the crystal form of claim 1 comprising
    (a) obtaining a crystal form of any of claims 13-20; and
    (b) mixing it with one or more pharmaceutically acceptable carrier.

23. A pharmaceutical preparation comprising the crystal form of claim 1 and a pharmaceutically acceptable carrier.

* * * * *